(12) United States Patent
Brockway et al.

(10) Patent No.: US 9,198,591 B2
(45) Date of Patent: Dec. 1, 2015

(54) INTRODUCER FOR A MINIMALLY INVASIVE PHYSIOLOGIC PARAMETER RECORDER

(75) Inventors: Brian P. Brockway, Shoreview, MN (US); Perry A. Mills, St. Paul, MN (US)

(73) Assignee: Greatbatch Ltd., Clarence, NY (US)

( * ) Notice: Subject to any disclaimer, the term of this patent is extended or adjusted under 35 U.S.C. 154(b) by 490 days.

(21) Appl. No.: 13/613,419

(22) Filed: Sep. 13, 2012

(65) Prior Publication Data

US 2013/0012800 A1    Jan. 10, 2013

Related U.S. Application Data

(62) Division of application No. 13/465,314, filed on May 7, 2012, now Pat. No. 8,280,499, which is a division of application No. 12/362,812, filed on Jan. 30, 2009, now Pat. No. 8,180,438.

(60) Provisional application No. 61/097,826, filed on Sep. 17, 2008, provisional application No. 61/024,875, filed on Jan. 30, 2008.

(51) Int. Cl.
*A61B 5/042* (2006.01)
*A61N 1/05* (2006.01)
*A61N 1/372* (2006.01)
(Continued)

(52) U.S. Cl.
CPC ............ *A61B 5/042* (2013.01); *A61N 1/0504* (2013.01); *A61N 1/375* (2013.01); *A61N 1/3787* (2013.01); *A61N 1/37229* (2013.01); *A61B 5/0031* (2013.01); *A61B 5/7232* (2013.01); *A61B 2560/063* (2013.01); *A61B 2560/066* (2013.01); *A61N 1/3756* (2013.01)

(58) Field of Classification Search
CPC ................. A61B 2560/063; A61B 2560/066; A61B 5/042; A61B 17/3468; A61B 2017/3445
USPC ............. 606/108, 129, 190; 128/899; 607/37
See application file for complete search history.

(56) References Cited

U.S. PATENT DOCUMENTS 3,943,936 A  3/1976  Rasor et al.
4,453,537 A  6/1984  Spitzer
(Continued)

FOREIGN PATENT DOCUMENTS

WO  8002231  10/1980
WO  2004041124  5/2004

OTHER PUBLICATIONS

International Search Report dated Apr. 15, 2009.

*Primary Examiner* — Todd Manahan
*Assistant Examiner* — Casey B Lewis
(74) *Attorney, Agent, or Firm* — Michael F. Scalise

(57) ABSTRACT

An implantable monitoring device includes a flexible lead body that includes at least one sensing element. The device also includes a rigid main body connected to the flexible lead body at an attachment point. The rigid main body is generally centered about a longitudinal axis defined by the flexible lead body when the lead body is unflexed. The device further includes a measurement circuit, which is housed within the rigid main body and electrically coupled to the at least one sensing element of the flexible lead body and at least another sensing element on an outside surface of the rigid main body. The measurement circuit is configured to measure a potential difference between the at least one sensing element of the flexible lead body and the at least another sensing element of the main body.

20 Claims, 29 Drawing Sheets

(51) Int. Cl.
*A61N 1/375* (2006.01)
*A61N 1/378* (2006.01)
*A61B 5/00* (2006.01)

(56) References Cited

U.S. PATENT DOCUMENTS

| | | | |
|---|---|---|---|
| 4,687,469 A | 8/1987 | Osypka | |
| 4,716,903 A | 1/1988 | Hansen et al. | |
| 4,974,600 A | 12/1990 | Reyes | |
| 5,113,869 A | 5/1992 | Nappholz et al. | |
| 5,269,326 A | 12/1993 | Verrier | |
| 5,313,953 A | 5/1994 | Yomtov et al. | |
| 5,324,312 A * | 6/1994 | Stokes et al. | 607/37 |
| 5,441,504 A * | 8/1995 | Pohndorf et al. | 606/129 |
| 5,645,586 A | 7/1997 | Meltzer | |
| 5,741,211 A | 4/1998 | Renirie et al. | |
| 5,833,603 A | 11/1998 | Kovacs et al. | |
| 5,987,352 A | 11/1999 | Klein et al. | |
| 5,993,472 A * | 11/1999 | Hermann et al. | 606/192 |
| 6,285,897 B1 | 9/2001 | Kilcoyne et al. | |
| 6,347,245 B1 | 2/2002 | Lee et al. | |
| 6,436,068 B1 | 8/2002 | Bardy | |
| 6,445,952 B1 | 9/2002 | Monrodt et al. | |
| 6,480,733 B1 | 11/2002 | Turcott | |
| 6,496,715 B1 | 12/2002 | Lee et al. | |
| 6,699,200 B2 | 3/2004 | Cao et al. | |
| 6,950,705 B2 | 9/2005 | Bardy et al. | |
| 7,107,093 B2 | 9/2006 | Burnes | |
| 7,107,103 B2 | 9/2006 | Schulman et al. | |
| 7,212,849 B2 | 5/2007 | Zhang et al. | |
| 7,299,086 B2 | 11/2007 | McCabe et al. | |
| 2001/0047314 A1 | 11/2001 | Linberg | |
| 2002/0035381 A1 * | 3/2002 | Bardy et al. | 607/4 |
| 2003/0004564 A1 | 1/2003 | Elkins et al. | |
| 2003/0191504 A1 | 10/2003 | Meadows et al. | |
| 2005/0027282 A1 * | 2/2005 | Schweikert et al. | 604/523 |
| 2006/0122676 A1 * | 6/2006 | Ko et al. | 607/116 |
| 2006/0217779 A1 | 9/2006 | Ransbury et al. | |
| 2007/0016089 A1 | 1/2007 | Fischell et al. | |
| 2007/0162101 A1 * | 7/2007 | Burgermeister et al. | 623/1.11 |
| 2008/0004569 A1 * | 1/2008 | McCrystle et al. | 604/104 |
| 2008/0249379 A1 | 10/2008 | Furman | |
| 2012/0191106 A1 * | 7/2012 | Ko et al. | 606/129 |

\* cited by examiner

INTRODUCER FOR A MINIMALLY INVASIVE PHYSIOLOGIC PARAMETER RECORDER

CROSS-REFERENCE TO RELATED APPLICATIONS

This application is a divisional of U.S. patent application Ser. No. 13/465,314, filed on May 7, 2012, now U.S. Pat. No. 8,280,499, which is a divisional of U.S. patent application Ser. No. 12/362,812, filed on Jan. 30, 2009, now U.S. Pat. No. 8,180,438 to Brockway et al. and entitled "Minimally Invasive Physiologic Parameter Recorder and Introducer System" which claims priority from U.S. Provisional Patent Application Ser. No. 61/024,875, filed on Jan. 30, 2008, and entitled "Injectable Physiologic Parameter Recorder," and from U.S. Provisional Patent Application Ser. No. 61/097,826, filed on Sep. 17, 2008, and entitled "Introducer System for Minimally Invasive Physiologic Parameter Recorder," and hereby incorporates by reference the contents of each case in its entirety.

TECHNICAL FIELD

This disclosure relates to implantable monitoring devices, and implantation systems and methods for implanting the monitoring devices at a subcutaneous implant location.

BACKGROUND

Implantable devices that monitor cardiac physiologic activity are frequently implanted subcutaneously under a patient's skin of the chest. An implantable loop recorder is an example of a device that may be implanted in this fashion. The implanted device may be leadless or may include subcutaneous leads. Two such devices are leadless and have a rigid rectangular shape. Another device, the Sleuth, is shaped like a small pacemaker, and includes a flexible lead extending from a header of the device. FIG. 1 shows an example of the Sleuth device. These devices can be used to record an electrocardiogram (ECG) signal for the patient.

To implant the Sleuth device, a 25 mm incision is made, a subcutaneous pocket is formed near the incision, and a tunnel is formed to extend away from the pocket for placement of the flexible lead using a tool or finger. The device may be inserted through the incision and placed in the subcutaneous pocket, tested for proper operation, and repositioned if necessary. The incision is then closed.

Implanting leaded devices in this manner may be difficult, especially for physicians who are not skilled in device implantation. If the device is improperly implanted, undesirable complications for the patient or suboptimal device performance may result. In addition, tearing of tissue during formation of the pocket and tunnel, for example, may result in tissue bleeding that requires appropriate steps during surgery to avoid hematoma. In addition, it may be necessary to employ fluoroscopy to assure that the flexible lead is properly positioned under the skin. If not properly positioned, the lead may require repositioning to obtain an optimal ECG signal. This may extend the surgery duration, which may increase risk of infection and trauma, as well as expense. A need exists for an improved device shape and associated insertion system for a simpler approach to insertion, shorter insertion time, reduced risk of complications, reduced expense, and a reduced need for expensive equipment, such as fluoroscopy, during device placement.

SUMMARY

In a first general aspect, an implantable monitoring device includes a flexible lead body that includes at least one sensing element. The device also includes a rigid main body connected to the flexible lead body at an attachment point. The rigid main body is generally centered about a longitudinal axis defined by the flexible lead body when the lead body is unflexed. The device further includes a measurement circuit, which is housed within the rigid main body and electrically coupled to the at least one sensing element of the flexible lead body and at least another sensing element on an outside surface of the rigid main body. The measurement circuit is configured to measure a potential difference between the at least one sensing element of the flexible lead body and the at least another sensing element of the main body.

In various implementations, a portion of the rigid main body of the device may taper from a first width to a second width narrower than the first width. The portion may taper symmetrically about a longitudinal axis of the rigid main body. The portion may taper approximately linearly from the first width to the second width, or may taper non-linearly from the first width to the second width. A first portion of the rigid main body may taper approximately linearly from a first width to a second width narrower than the first width, and a second portion of the rigid main body may taper non-linearly from a third width to a fourth width narrower than the third width. The rigid main body may include at least a first housing section that is hermetically sealed and a second housing section that is not hermetically sealed. A width of a proximal section of the second housing section may be substantially greater than a width of a distal section of the second housing. The device may also include loop member on a proximal portion of the rigid body. The loop member may be used to suture the device to body tissue, and a withdrawal force may be applied to the loop member extract the device is extracted from an implant location.

In a second general aspect, an implantable monitoring device includes a flexible lead body. The device also includes a rigid main body connected to the flexible lead body at an attachment point. The rigid main body is generally centered about a longitudinal axis defined by the flexible lead body when the lead body is unflexed. The rigid main body includes a tapered portion proximate the lead body, and the tapered portion has smaller width nearer the lead body. The device further includes a measurement circuit, housed within the rigid main body and electrically coupled to at least one sense electrode on the flexible lead body and at least another sense electrode on an outside surface of the rigid main body. The measurement circuit is configured to measure a potential difference between the at least one sense electrode on the flexible lead body and the at least another sense electrode on the main body.

In a third general aspect, a method of implanting a monitoring device subcutaneously in a body of a patient includes assembling an introducer, which includes a sheath and a semi-flexible insert, by placing the semi-flexible insert within the sheath. The semi-flexible insert is sized and shaped at least in part to match a size and shape of the monitoring device. The semi-flexible insert and the monitoring device each include a tapered section that tapers from a first width at a proximal end of the section to a second width, smaller than the first width, at a distal end of the section. The method also includes introducing a distal end of the introducer through an incision in the patient's skin to a desired subcutaneous implant location site beneath the patient's skin. The method further includes withdrawing the semi-flexible insert from the sheath without substantially disturbing the position of the sheath at the desired subcutaneous implant location site, and inserting the monitoring device into the sheath. The method further includes withdrawing, in a direction opposite that which it was introduced, the sheath from the implant location site while applying pressure to the monitoring device, wherein an external surface of the sheath splits along an axis as the sheath surface is forced against the tapered section of the monitoring device while the sheath is being withdrawn.

In various implementations, at least a portion of the sheath may be sized and shaped in proportion to a corresponding portion of the semi-flexible insert. The distal end of the introducer may deflect upon contacting a surface of a muscle layer and slide across the surface of the muscle layer without penetrating the muscle layer. The external surface of the sheath may include a surface modification along at least a portion of the axis, and the surface modification may reduce a tensile strength of the external surface of the sheath along the axis.

In a fourth general aspect, an introducer system for implanting, within a body of a patient, a monitoring device that includes a tapered section that tapers from a first width at a proximal end of the section to a smaller second width at a distal end of the section, at a subcutaneous implant location site within the body of the patient, includes a semi-flexible insert. At least a portion of the semi-flexible insert is substantially sized and shaped to match a portion of the monitoring device, including the tapered section. The system also includes a sheath sized and shaped to separately receive, within a space defined by an internal surface of the sheath, the semi-flexible insert and the monitoring device. The sheath is splittable along a longitudinal axis of the sheath to facilitate removal of the sheath from the subcutaneous implant location site.

In various implementations, a distal portion of the sheath may be sized and shaped in proportion to a corresponding distal portion of the semi-flexible insert. The sheath may be more flexible than the semi-flexible insert, and a distal portion of the semi-flexible insert may have sufficient rigidity to avoid substantial deflection when directed through a fatty tissue layer of the patient, and sufficient flexibility to, upon contacting a surface of a muscle layer of the patient, deflect and slide across the surface of the muscle layer without penetrating the muscle layer. An external surface of the sheath may include a surface modification along at least a portion of the longitudinal axis, and the surface modification may reduce a tensile strength of the external surface of the sheath along the longitudinal axis. The system may also include a rod member preformed to define an arc angle, where the rod member may be more rigid than the semi-flexible insert, and where the semi-flexible insert may define a cavity capable of receiving the rod member.

In a fifth general aspect, a method of implanting an implantable monitoring device—which includes a rigid main body and a flexible extension that, when unflexed, is substantially collinear with a longitudinal axis of the rigid main body—in a subcutaneous implant region of a patient includes introducing an insert device to the subcutaneous region of the patient. The insert device has an internal chamber that is generally in the shape of at least a portion of the implantable monitoring device. The method also includes inserting, after the insert device has been introduced to the subcutaneous region, the implantable monitoring device to the internal chamber of the insert device. The method further includes removing the insert device from the subcutaneous region while leaving the implantable monitoring device at the subcutaneous region.

In various implementations, removing the insert device from the subcutaneous region includes withdrawing, in a direction opposite that which it was introduced, the insert device from the subcutaneous region while applying pressure to the monitoring device, where the insert device includes a surface modification to reduce a tensile strength of the insert device. The subcutaneous region may be above a pectoral fascia of the patient. At least a portion of the subcutaneous region may be below a pectoral fascia of the patient, or the entire subcutaneous region may be below the pectoral fascia.

The details of one or more implementations are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
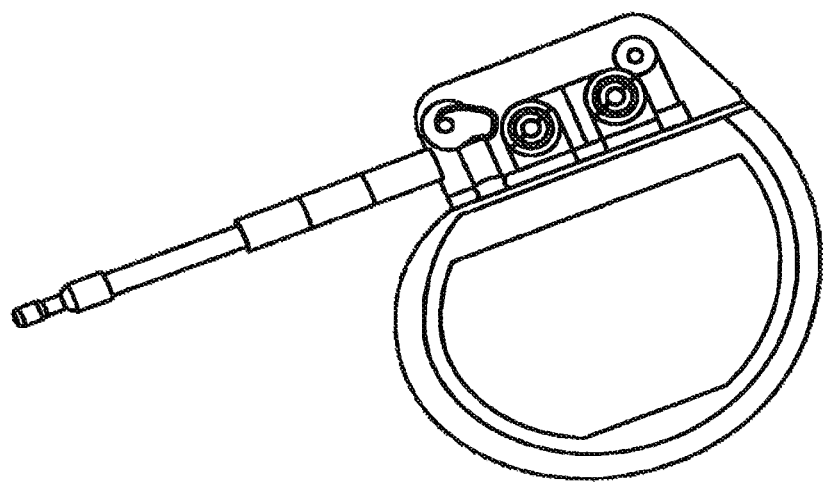
FIG. 1 is a prior art physiologic signal monitoring device.
Figure 2:
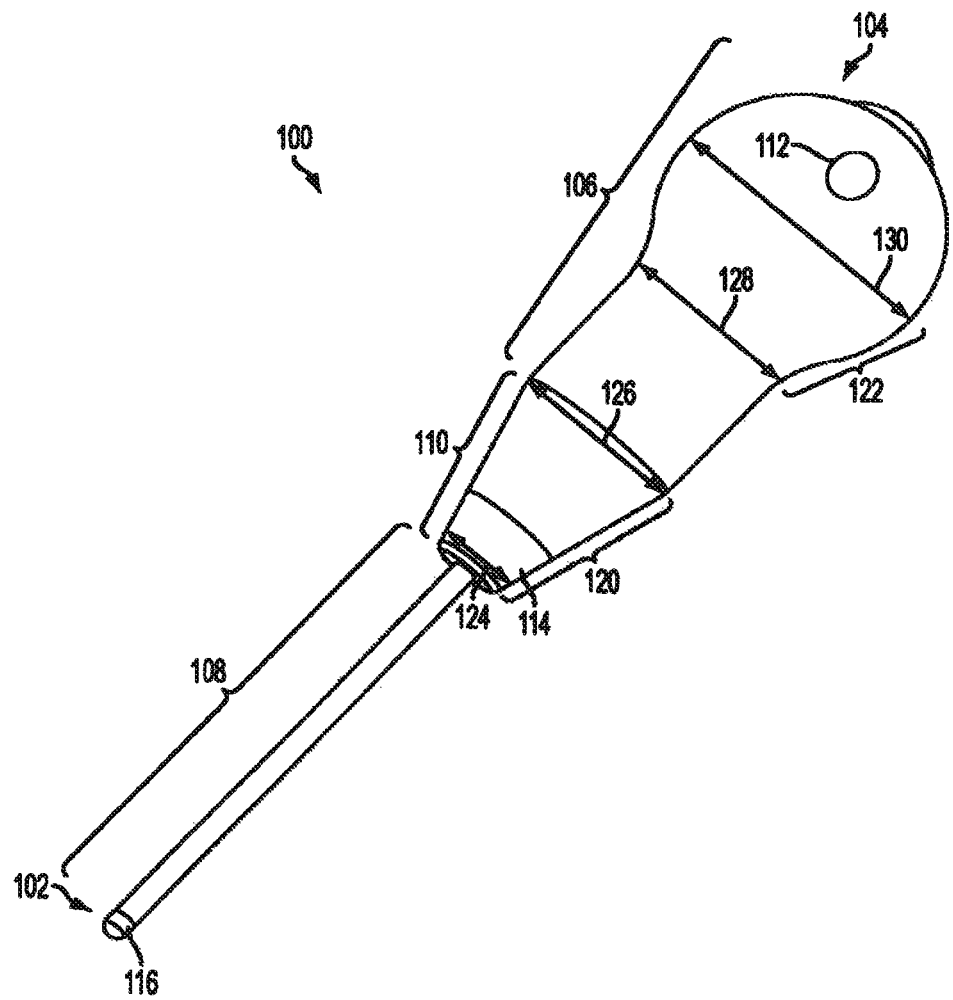
FIG. 2 is an elevation view of an exemplary implantable device that can be subcutaneously implanted under a patient's skin.

FIG. 2 is an elevation view of an exemplary implantable device 100 that can be subcutaneously implanted under a patient's skin. Prior to implantation, an introducer system can be used to create and prepare an implant location site for the implantable device 100. Using implementations of the devices and techniques discussed herein, the implantable device 100 may be implanted in a minimally invasive fashion that minimizes an incision size for insertion, minimizes trauma to body tissue during formation of an implant channel for the implantable device 100, minimizes risk of puncture or intrusion upon a muscle layer, intercostal space or body organ, and provides a fitted implant location closely tailored to actual device dimensions. Because incision size may be reduced as compared to previous implant techniques, a scar from the insertion may be less noticeable. Also, by forming an appropriately sized pocket for the implantable device 100, a risk of hematoma may be reduced. Further, the devices, systems and techniques disclosed herein may significantly reduce the time required for implantation, and may mitigate the need for fluoroscopy, thereby reducing the cost associated with the implantation procedure. Moreover, the simplicity of the approach described here may make implantation feasible in a procedure room or doctor's office, and may provide for consistently good results when implanted by physicians who lack experience and skills in placing implantable devices. For at least these reasons, physicians may prefer the systems, devices and techniques discussed herein when compared to presently available implant methods and devices.

By way of example, the device 100 may be a minimally invasive implantable monitoring device that senses and records a physiologic parameter, such as electrical activity of the heart, within a body of a patient. In some implementations, the device 100 is an implantable monitoring device that senses and records a physiologic parameter, such as an electrocardiogram (ECG) signal, within the body of the patient and wirelessly transmits information associated with the physiologic parameter to an external device. Such a monitoring-only device that records cardiac electrical information may be implanted in a human patient for a relatively short period of time, such as a few months for example.

Other physiologic parameters or combinations of parameters, such as other electrical signals (e.g., EEG signal, ENG signal, neural signal, bio-impedance signal), mechanical signals (e.g., blood pressure signal, blood flow signal), chemical signals (e.g., glucose), temperature and the like may similarly be recorded by the device 100 in various implementations. The description that follows will focus without limitation on implementations where the device 100 is used to monitor a subcutaneous ECG signal, but in other implementations such monitoring could be combined with or substituted by other monitoring functions, such as arterial blood pressure monitoring, for example.

Figure 17:
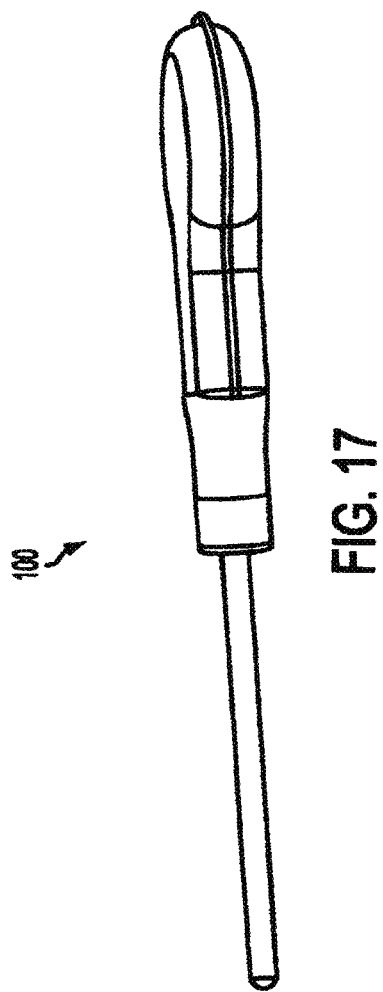
FIG. 17 is an elevation view of an exemplary implantable device.

In some implementations, the device 100 may be relatively small, and may be sized and shaped for convenient implantation within a body of a patient, such as at a subcutaneous implant site, for example, in a pectoral region of a human patient, as will be discussed in more detail below. As can be seen with reference to FIG. 2, the device 100 has generally a flat shape, and includes a distal end 102 and a proximal end 104. FIG. 17 is another elevation view of the implantable device 100, and illustrates the generally flat shape of the device 100. Using an introducer system that will be described more fully below, the device 100 may be introduced distal-end-first at an appropriate implant site following formation of a preparatory channel using the introducer system. In other implementations, the device 100 may be directly inserted to a subcutaneous implant location, without using the introducer system.

The exemplary device 100 generally includes three sections: a proximal section 106, a distal extension 108, and a midsection 110 between the proximal section 106 and the distal extension 108. In various implementations, the proximal section 106 may comprise a hermetic housing, the midsection 110 may comprise a non-hermetic housing, and the distal extension 108 may comprise a flexible lead.

Figure 18:
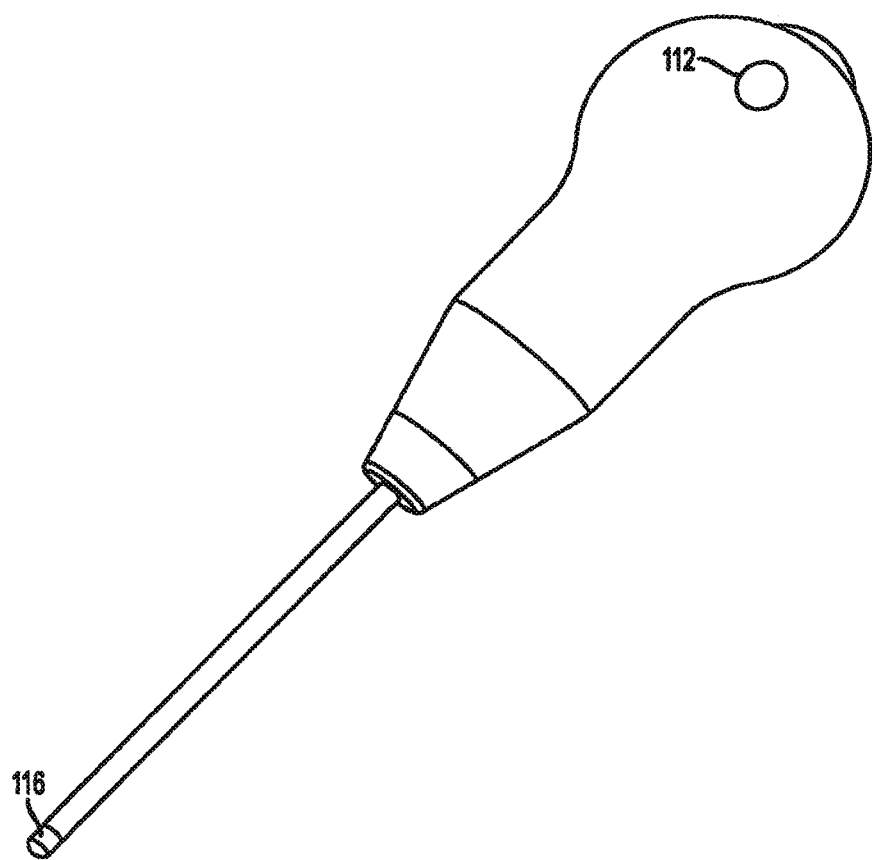
FIG. 18 is an elevation view of another exemplary implantable device that can be subcutaneously implanted under a patient's skin.

The device 100 may include one or more electrodes for electrically interfacing to surrounding tissue for the purpose of sensing electrical activity. In some implementations, device 100 includes two electrodes. For example, FIG. 18 shows an implantable device having a proximal electrode 112 and a distal electrode 116, and may measure a potential difference (e.g., a subcutaneous ECG signal) between the proximal and distal electrodes 112, 116. The electrodes 112 and 116 are each near a longitudinal end of the device 100. This placement may maximize signal vector length of a measured physiologic signal. In general, measured amplitude of a sensed physiologic signal, such as an ECG signal, will vary with device placement and orientation within the patient. Sensed signal amplitude may also be related to separation distance between the measuring electrodes. Positioning the electrodes 112, 116 near opposite ends (e.g., near opposite longitudinal ends) of the device 10 may maximize the amplitude of the sensed physiologic signal for a given device length, which may lead to better measurement results.

In other implementations, device 100 includes three electrodes, though any suitable number (one, two, three, four, five, etc.) may be used in other implementations.

Referring again to FIG. 2, a proximal electrode 112 comprises an exterior surface of the proximal section 106. A midsection electrode 114 is located on an exterior surface of the midsection 110, and is a circumferential or ring electrode in this implementation. A distal electrode 116 comprises a tip electrode in the depicted implementation, and is positioned near the distal end 102 of the distal extension 108. The device may measure a potential difference between any two of the electrodes 112, 114, 116. For example, the device 100 may measure a potential difference between the proximal electrode 112 and the distal electrode 116, between the proximal electrode 112 and the midsection electrode 114, or between the midsection electrode 114 and the distal electrode 116. In an implementation, the device senses two vectors: a first vector between electrode 112 and electrode 116, and a second vector between electrode 114 and electrode 116. In some implementations, one or more of the electrodes may comprise excitation electrodes or combination excitation/sense electrodes. As an example, the device may measure a bio-impedance for diagnostic purposes by injecting a known current between two electrodes and measuring a resulting voltage between two electrodes. In these implementations, the device 100 may similarly inject, a current between any two of the electrodes. The electrodes may comprise a conductive material such as titanium in some implementations, and any appropriate style of electrode may be used for any of the electrode locations. In various implementations, the subsequent voltage measurement may occur across the two electrodes used to inject the current, across one electrode used to inject current and another electrode that was not involved with the current injection, or across two electrodes different from the current injection electrodes.

A first end of the flexible lead 108 is attached at a fixation point to the midsection 110, and may generally flex or bend about the fixation point, according to some implementations.

The midsection 110 thus stabilizes the flexible lead 108, yet allows it to bend and flex about the fixation point to conform to body tissue channel formation and subsequent tissue movement and flexing as the patient's muscles contract and expand during daily activities. For example, with some implementations it may be desirable to implant the device 100 such that the lead 108 extends collinearly with the proximal section 106 and midsection 110, as shown in FIG. 2. In other implementations, it may be desirable to implant the device 100 such that the lead 108 is flexed. In general, the flexible lead 108 may bend at any appropriate angle with respect to the fixation point, and in any appropriate direction. For example, with reference again to FIG. 17 and the relatively flat profile presented by the rigid body portion of the device, the lead may bend in a direction above or below a plane defined by a longitudinal axis of the rigid body, and may do so at any appropriate angle with respect to the plane. For example, the lead may assume a curved orientation, as will be described below, so that an appropriate vector angle between an electrode on the lead and an electrode on the body of the device may be realized with respect to a plane or vector defined by the device, or another measurement vector, according to some implementations.

Referring again to FIG. 2, the device 100 may generally be provided with a substantially flat cross-section to achieve good biocompatibility and patient comfort, and so proximal section 106 may readily accommodate electronic circuits and components that have flat construction, such as circuit boards and components or integrated circuits that attach thereto, including certain batteries, for example. Such a shape, in combination with the improved implant site location formation methods discussed herein, may also be conducive to physiologic measurements, in that the device may be less likely to rotate about its longitudinal axis. For example, device migration or rotation may be minimized, which may permit better measurement results as electrode surfaces may move less with respect to contacting tissue. As such, a preferred orientation established at implantation time may be maintained. Maintaining desired device location and orientation at the implant site location may also improve telemetry performance and power reception performance in implementations utilizing a rechargeable battery, as challenges associated with uncontrolled orientation or misalignment may be avoided or minimized.

Figure 3:
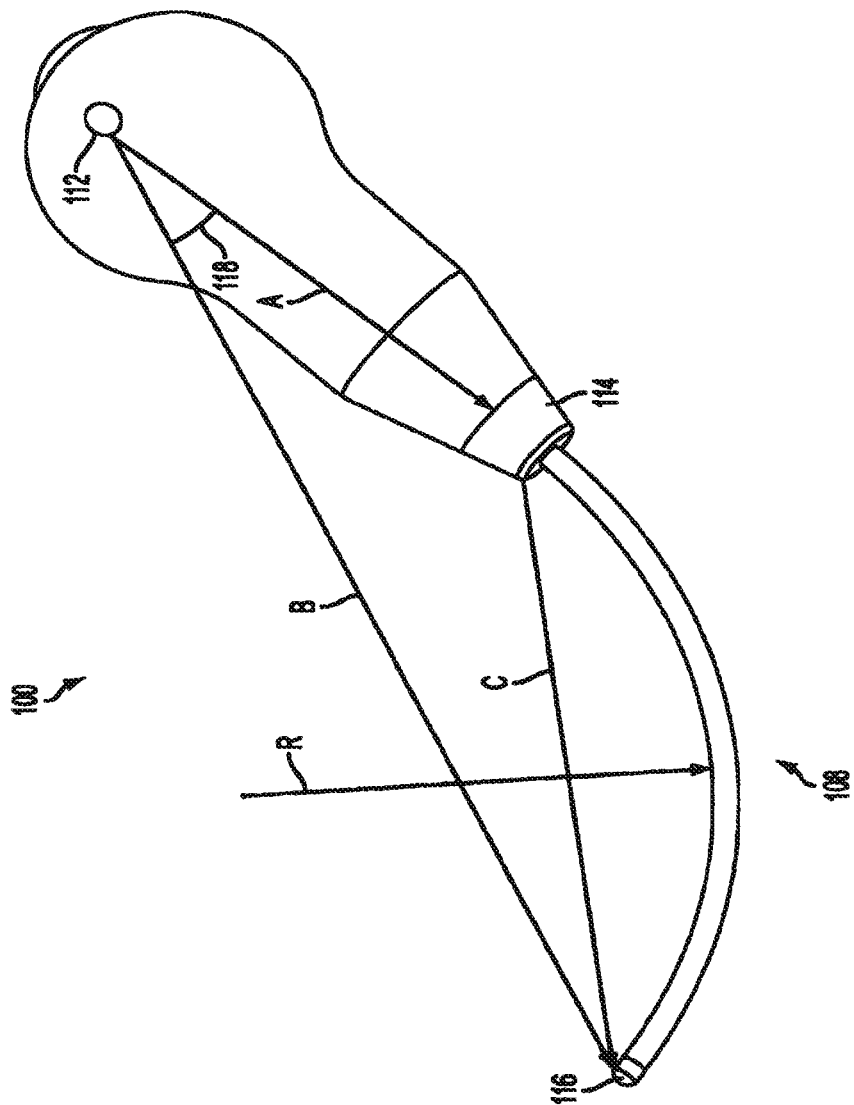
FIG. 3 is an elevation view of the exemplary implantable device of FIG. 2 with a curved lead orientation.

FIG. 3 is an elevation view of the exemplary implantable device of FIG. 2 with a flexed or curved lead orientation. Using the techniques, systems, and devices described here, the device 100 may be implanted within a body such that the lead 108 has a curved orientation. As shown, the lead 108 has a radius of curvature "R," and may conform to surrounding tissue at the implant location. Curved lead orientations with non-circular arcs may also be used, and implantation pockets for any appropriate lead arc angle may be formed at an implant location site, as will be described more fully below. With such an orientation, non-collinear measurement vectors may be realized between the device electrodes 112, 114, and 116. For example, a first measurement vector "A" may be defined between the proximal electrode 112 and the midsection electrode 114, and a second measurement vector "B" may be defined between the proximal electrode 112 and the distal electrode 116. In some implementations, an angle 118 of thirty degrees or more may separate the measurement vectors A and B. Similarly, a third measurement vector "C" may be defined between the midsection electrode 114 and the distal electrode 116. In implementations where the device 100 is implanted to have two or more non-collinear ECG measurement vectors, improved measurement performance may result. For example, multiple vectors can be useful in assessing ECG morphology and for noise reduction. As such, multiple-vector measurement of subcutaneous ECG may provide a more global assessment of cardiac condition. Also, depending on device orientation and body tissue interface characteristics, in some cases one of the measurement vectors may provide weak signal reception, while another measurement vector may provide comparatively strong signal reception. In this case, having multiple measurement vector alternatives provides redundancy, which may make the measurement system more robust. As will be described more fully below, an appropriate measurement angle between any two measurement vectors may be selected based on a suitable radius of curvature "R" or arc angle for lead 108, which may be varied by appropriate selection of a curved insert pin as part of an introducer system implantation process.

Referring again to FIG. 2, the implantable device 100 includes a first tapered section 120 and a second tapered section 122. The tapered sections 120, 122 may facilitate ease of insertion under the skin, and may promote, in combination with the introducer system to be described below, a snug-fitting implant site location for the device 100. The first tapered section 120, generally corresponding to the midsection 110 in this implementation, widens linearly from a first width 124 at the distal-end side of the section to a larger second width 126 at the proximal-end side of the section (or conversely tapers from the second width 126 to the first width 124). The second tapered portion 122 also widens from a distal-facing first width 128 to a proximal-facing larger second width 130 (or conversely tapers in the opposite direction), but does so non-linearly, in arcuate fashion. In this example, width 126 is approximately equal to width 128.

Figure 4:
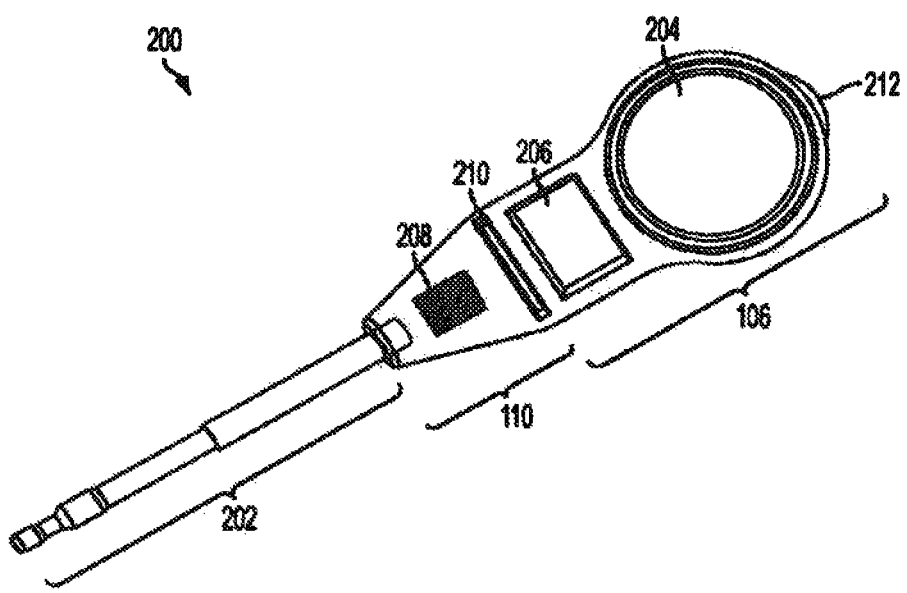
FIG. 4 is a top view of an exemplary implantable device showing selected components housed within the device.

FIG. 4 is a top view of an exemplary implantable device 200 showing selected components housed within the device. Like the implantable device 100 of FIG. 2, device 200 includes proximal section 106 and midsection 110, but includes a different style distal extension 202 in this implementation, though the lead 108 from the FIG. 2 implantable device 100 could alternatively be used. As described above, the proximal section 106 may comprise an external surface formed of a hermetic material, such as a metal or ceramic. The proximal section 106 may house a battery 204, which may be single-use or rechargeable in various implementations, and circuitry 206 (e.g., an electronics module) for performing actions consistent with the device's intended purpose. Without limitation, examples of actions that may be performed with some implementations of the device include measuring one or more physiologic signals, storing the measured signal(s) in memory within the device 100, processing collected data, wirelessly transmitting or receiving information to/from an external device, and others.

The midsection 110 may include a non-hermetic external surface, and may be designed to enclose or embed components suited for housing in a non-conductive enclosure, such as components that communicate by field or wave properties that may otherwise be impeded by a conductive housing. In this implementation, the midsection 110 houses an antenna 208 for wirelessly transmitting data to an external device or wirelessly receiving data from an external device. In some implementations, the non-hermetic section may be molded with a polymer such as urethane to avoid having a conductive housing that could attenuate telemetry signals transmitted from, or received by, the telemetry antenna 208. In various implementations, the non-hermetic section 110 may be radio-paque. In some implementations, the midsection 110 can include a charging coil (not shown in FIG. 4) that can be excited (e.g., with an external charging coil placed in proximity to the implant location) to recharge a rechargeable battery of the device. Hermetic feedthroughs 210 may be provided where electrical connections enter or exit the hermetic proximal section 106 from the non-hermetic midsection 110 to maintain hermeticity of the proximal section 106. In some cases, electrical connections through the interconnecting element 210 may take the form of a helix, which may provide a long flex life. The electrical connections may optionally be coated with parylene or other material to provide a secondary form-fitting barrier that may isolate each conductor. Protection offered by this secondary coating may especially benefit conductors carrying DC voltage, as factors such as dendrite growth that can adversely affect reliability may be minimized or prevented.

The distal extension 202 may be a flexible subcutaneous lead attached to the midsection 110 at one end. Like the lead 108 of the device 100 shown in FIG. 2, lead 202 may include one or more electrodes for measuring electrical activity or stimulating body tissue. In some implementations, the distal extension 202 can serve as the telemetry antenna for the device 200, and in these cases the depicted antenna 208 may be omitted. In some implementations, the telemetry antenna function is incorporated into the distal extension (lead) 202 independent from any ECG sensing lead functionality.

In general, extraction of devices (e.g., devices 100 or 200) according to any of the implementations discussed herein may include forming a small incision in the skin and grasping the device from a proximal end with an appropriate tool, such that it can be separated from attached tissue and removed. Some implementations include a feature on an exterior surface of the device to facilitate grasping of the device. For example, a retraction loop 212 near the proximal end of the device may be grasped or hooked in this fashion for ease of retraction. That is, at time of explant, a physician may grasp the loop 212, for example with a grasping tool, and apply an extraction force. In some implementations, the loop may be used as a suture hook to secure the device to tissue at a subcutaneous implant location.

Figure 5:
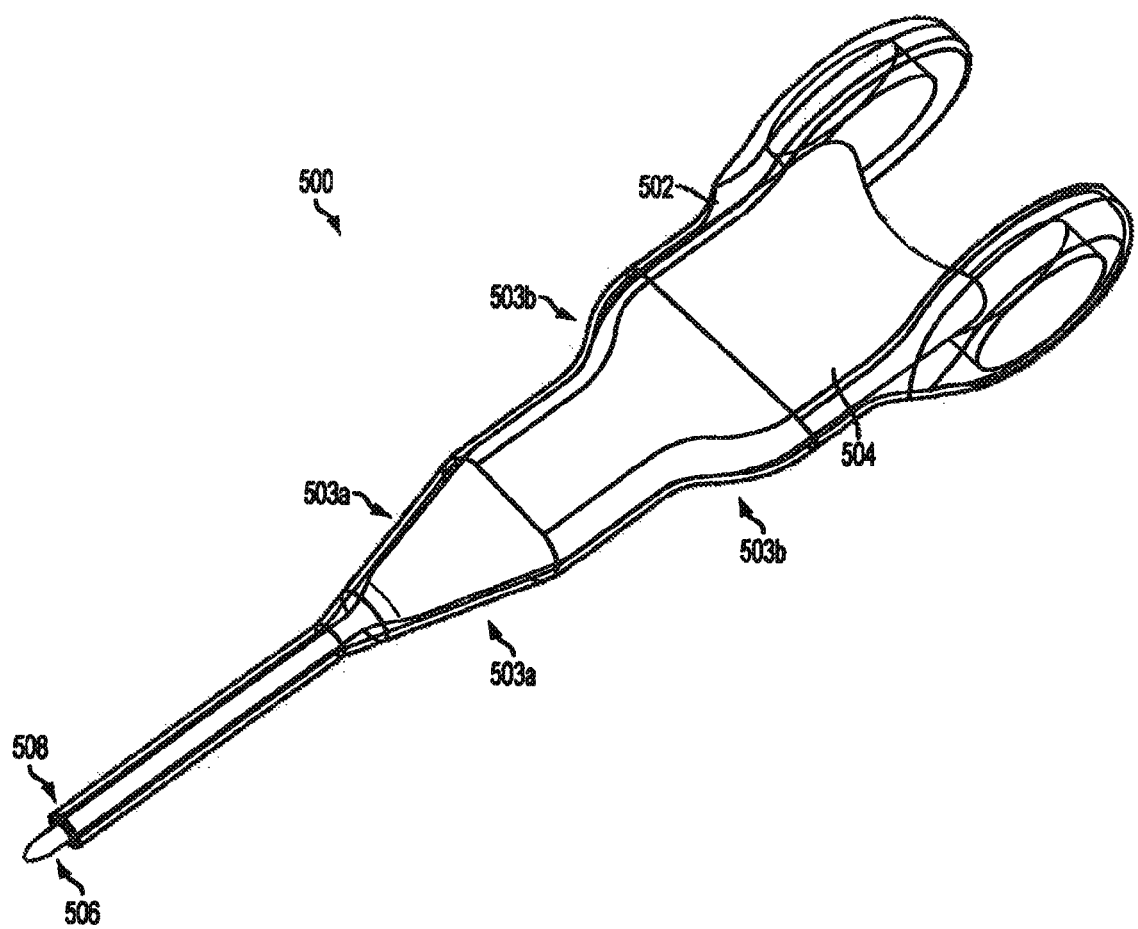
FIG. 5 is an elevation view an exemplary introducer system that may be used to introduce the implantable devices of FIGS. 2-4 to a subcutaneous implant site within a body.

FIG. 5 is an elevation view of an introducer system 500 that may be used to introduce any of the implantable devices discussed herein (e.g., devices 100, 200 of FIGS. 2-4) to a subcutaneous implant site within a body. In various implementations, the introducer system 500 includes a sheath 502 and a semi-flexible insert 504. The semi-flexible insert 504 may be placed within the sheath 502 (e.g., within a cavity defined by the sheath), as shown in FIG. 5, and a distal tip 506 of the semi-flexible insert 504 may protrude slightly (e.g., 1-5 mm) from a distal end 508 of the sheath 502. In an implementation, the distal tip 506 of the semi-flexible insert 504 may be substantially blunt. The sheath 502 and semi-flexible insert 504 may be introduced through an incision in the patient's skin and through a layer of fatty tissue below the skin. The distal end 506 of the semi-flexible insert 504 may initially create a channel through the body tissue as the introducer system 500 is introduced. Tapered portions 503 of the introducer system further assist in channel creation, as will be described more fully below.

As can be seen with reference to FIG. 5, portions of both the sheath 502 and the semi-flexible insert 504 have size and shape substantially similar to the size and shape of the implantable devices 100, 200 discussed above. The sheath 502 and semi-flexible insert 504 of the introducer system 500 can be used to create an implant channel and prepare an implant site location for the implantable device (e.g., device 100 or 200), where the implant site closely matches the size and shape of the implant device. Using the introducer system 500, the channel and implant location site may be created in a minimally invasive fashion that minimizes tissue disturbance and tissue trauma.

Figure 6:
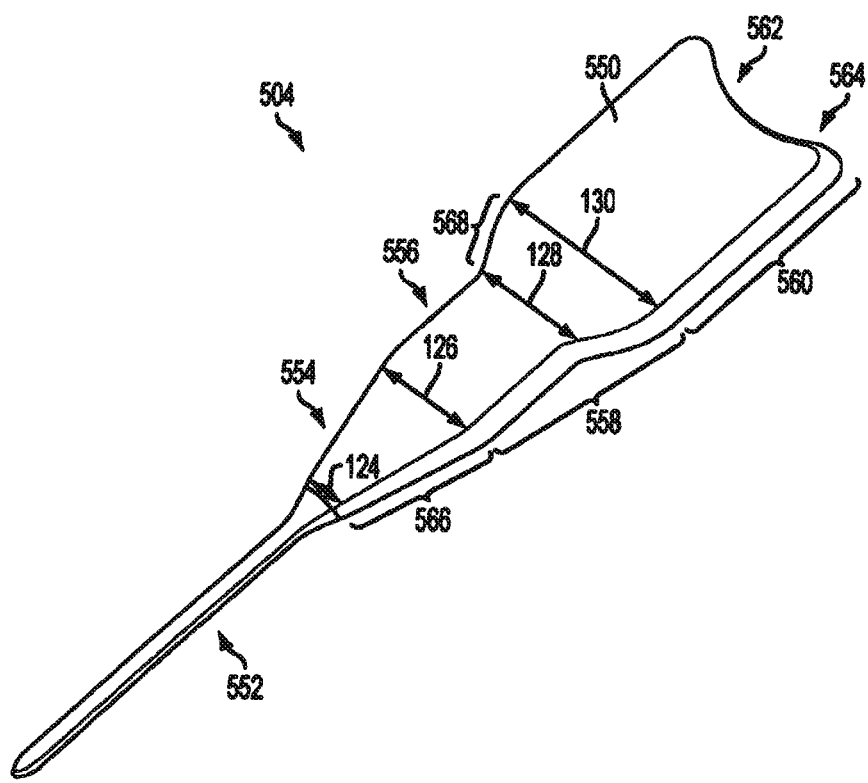
FIG. 6 is an elevation view of an exemplary semi-flexible insert.

FIG. 6 is an elevation view of an exemplary semi-flexible insert, such as the semi-flexible insert 504 depicted in FIG. 5. The semi-flexible insert 504 includes an external surface 550, portions of which are sized and shaped to generally match the size and shape of portions of the implantable device 100. For example, the semi-flexible insert 504 includes a distal portion 552 with generally the same size and shape as the distal extension 108 of the implantable device 100; a mid-portion 554 with generally the same size and shape as the midsection 110 of the implantable device 100; and a proximal portion 556 that includes a lower proximal portion 558 and an upper proximal portion 560. The lower proximal portion 558 has generally the same size and shape as the proximal section 106 of device 100 from the distal-facing side of the proximal section 106 to the point of maximum width of proximal section 106. A distal-facing surface 562 of the upper proximal portion 560 may define a depression 564 in some implementations. A physician may apply pressure to the distal-facing surface 562 of the upper proximal portion 560 (as by placing her thumb against the surface) and may direct the introducer system 500 to a desired implant location site.

The semi-flexible insert 504 may comprise a semi-flexible, semi-rigid polyethylene material in various implementations. In some implementations, the semi-flexible insert 504 is sufficiently flexible to deflect upon contacting a muscle layer during the introduction process. For example, as the introducer system 500 is inserted through an incision in the skin and through a fatty tissue layer below the skin, when the distal tip 506 (see FIG. 5) of the semi-flexible insert 504 contacts a muscle layer below the fatty tissue layer, which may generally be harder and more dense than the fatty tissue layer, the distal portion 552 of the semi-flexible insert 504 may deflect so that the introducer system slides across the top of the muscle layer rather than penetrating into the muscle layer. That is, as the introducer system 500 is urged through a fatty tissue layer of the body below the skin at an angle relative to the muscle layer, when the distal end of the system contacts the muscle layer, the system should deflect to slide across the muscle layer, substantially parallel to the muscle layer, even though the proximal end of the introducer system may continue to be urged at the same angle relative to the muscle layer. This may increase patient safety, as muscle layer or intercostal space puncture may be avoided even if the physician directs the introducer system at a steeper-than-appropriate angle with respect to the muscle layer. The semi-flexible insert 504 should nevertheless be rigid enough to provide direction and maintain its shape and orientation without substantial flexing as the introducer system 500 is introduced through the skin layer and the fatty tissue layer.

Figure 15:
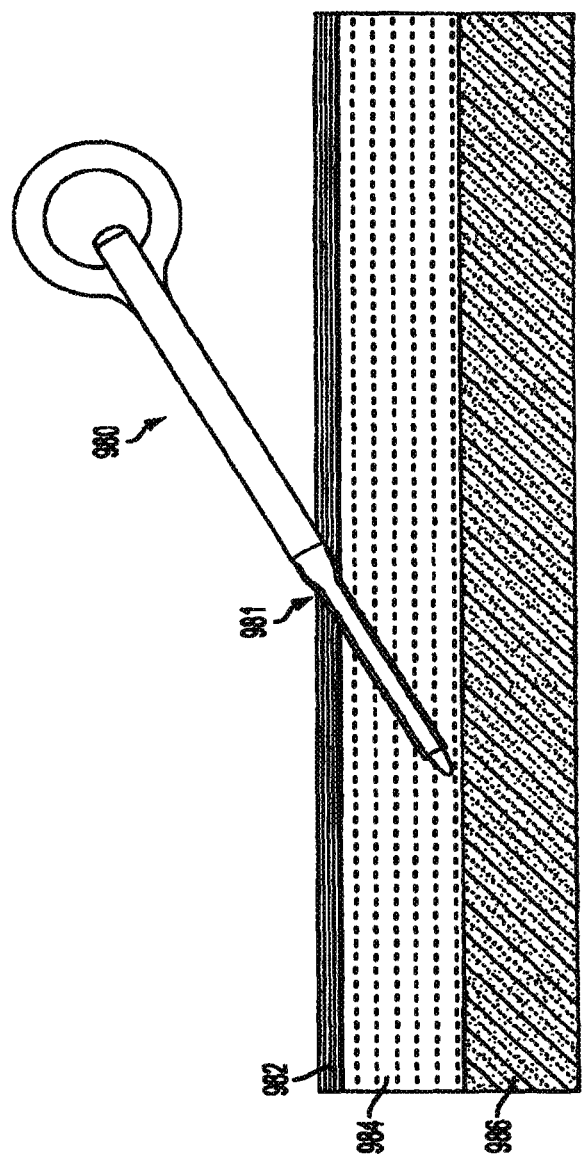
FIG. 15 is a view of an introducer system being introduced through an incision and a fatty tissue layer.

FIG. 15 is a view of an introducer system 980 being introduced through an incision 981 in a skin layer 982 and through a fatty tissue layer 984. As described above, the introducer system 980 may include a sheath (e.g., sheath 502) and a semi-flexible insert (e.g., semi-flexible insert 504), each of which may be sized and shaped in part to match or conform to a size and shape of an implantable device. In this fashion, an implant site location may be created that closely matches the size and shape of the implant device, for a snug-fitting pocket with residual tissue compression pressure on the implanted device to minimize risk of device migration and tissue bleeding.

Figure 16:
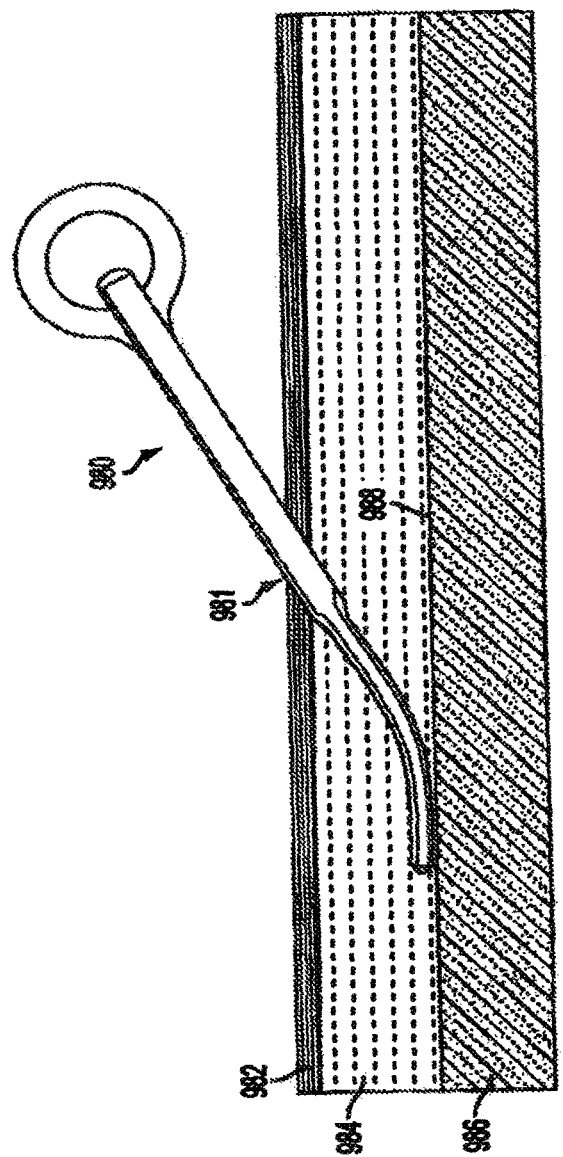
FIG. 16 is a view of the introducer system of FIG. 15 after a distal portion of the system has contacted a muscle layer.

As shown in FIG. 15, the distal end of the introducer system 980 is approaching a muscle layer 986 as the system is urged through the incision 981, skin layer 982, and fatty tissue layer 984, as by a physician. FIG. 16 is a view of the introducer system 980 of FIG. 15 after a distal portion of the system 980 has contacted the muscle layer 986. As shown in FIG. 16, the introducer system may deflect and slide along a top surface 988 of the muscle layer 986 without penetrating the muscle layer 986. When the introducer system 908 has been introduced to the desired implant site location, the semi-flexible insert may be withdrawn from the sheath and removed from the body through the incision 981, leaving the sheath in place at the implant site location. Next, the implantable device 100 may be inserted into the sheath at the implant site location, and the sheath may be withdrawn from the site, as will be discussed below.

Figure 20:
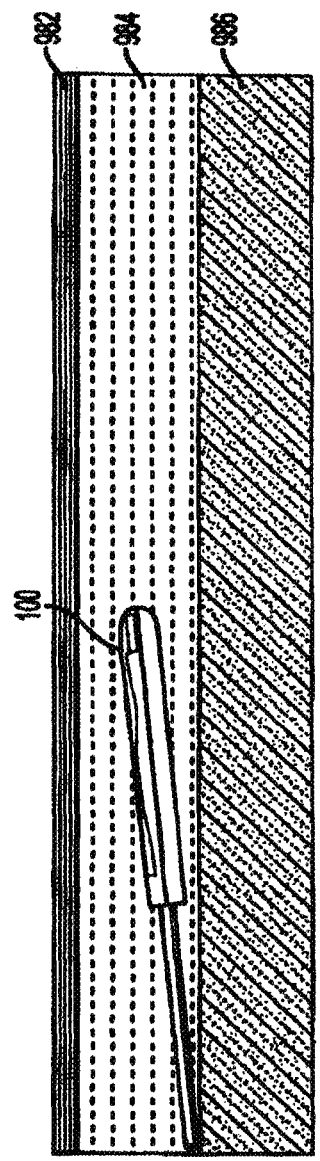
FIG. 20 is a view of a device implanted subcutaneously in a patient using the introducer system of FIGS. 15-16, FIGS. 21-22 are exterior views of an exemplary implantable device that includes at least two rigid sections separated by at least one flexible section.

FIG. 20 is a view of the device 100 implanted subcutaneously in a patient using the introducer system 980 of FIGS. 15-16. The implantable device 100 is positioned at an implant site location created by the introducer system 980 below the skin 982 within the layer of fatty tissue 984, just above the muscle layer 986. The implant site location size and shape is closely matched to the size and shape of the implant device 100 because of the size and shape of the sheath and semi-flexible insert (an optionally an insertion pin, described below) that comprise the introducer system 980.

As described above, the semi-flexible insert 504 includes a first tapered section 566 and a second tapered section 568. Like the implantable device, the tapered sections 566, 568 of the semi-flexible insert 504 include opposing lateral surfaces that are tapered. The first tapered section 566 widens linearly from a first width 124 at the distal-end side of the section 566 to a larger second width 126 at the proximal-end side of the section 566 (or conversely tapers from the second width 126 to the first width 124). The second tapered portion 568 also widens from a distal-facing first width 128 to a proximal-facing larger second width 130 (or conversely tapers in the opposite direction), but does so non-linearly, in arcuate fashion. In this example, width 126 is approximately equal to width 128. As such, the tapered portions 566, 568 of the semi-flexible insert 504 are sized and shaped to substantially match tapered portions 120, 122 of the implantable device 100, which may facilitate formation of a fitted implant location closely tailored to actual device dimensions.

Figure 7:
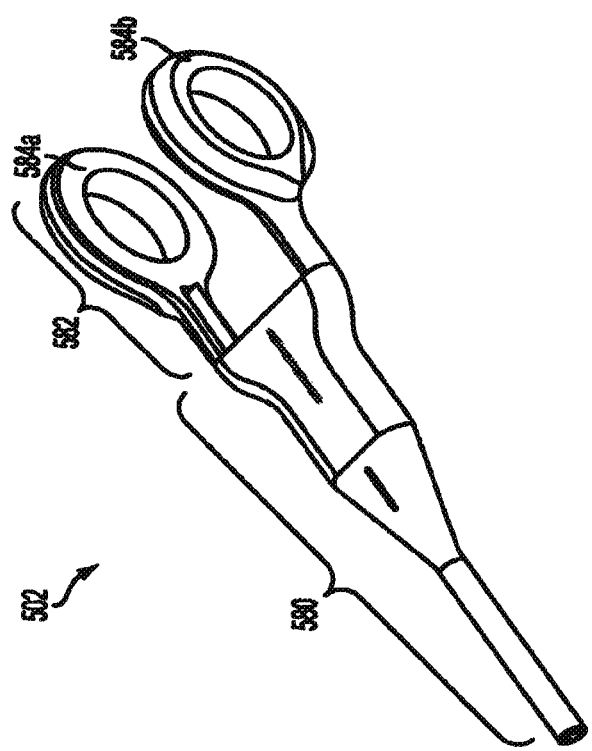
FIG. 7 is an elevation view of an exemplary sheath.
Figure 8:
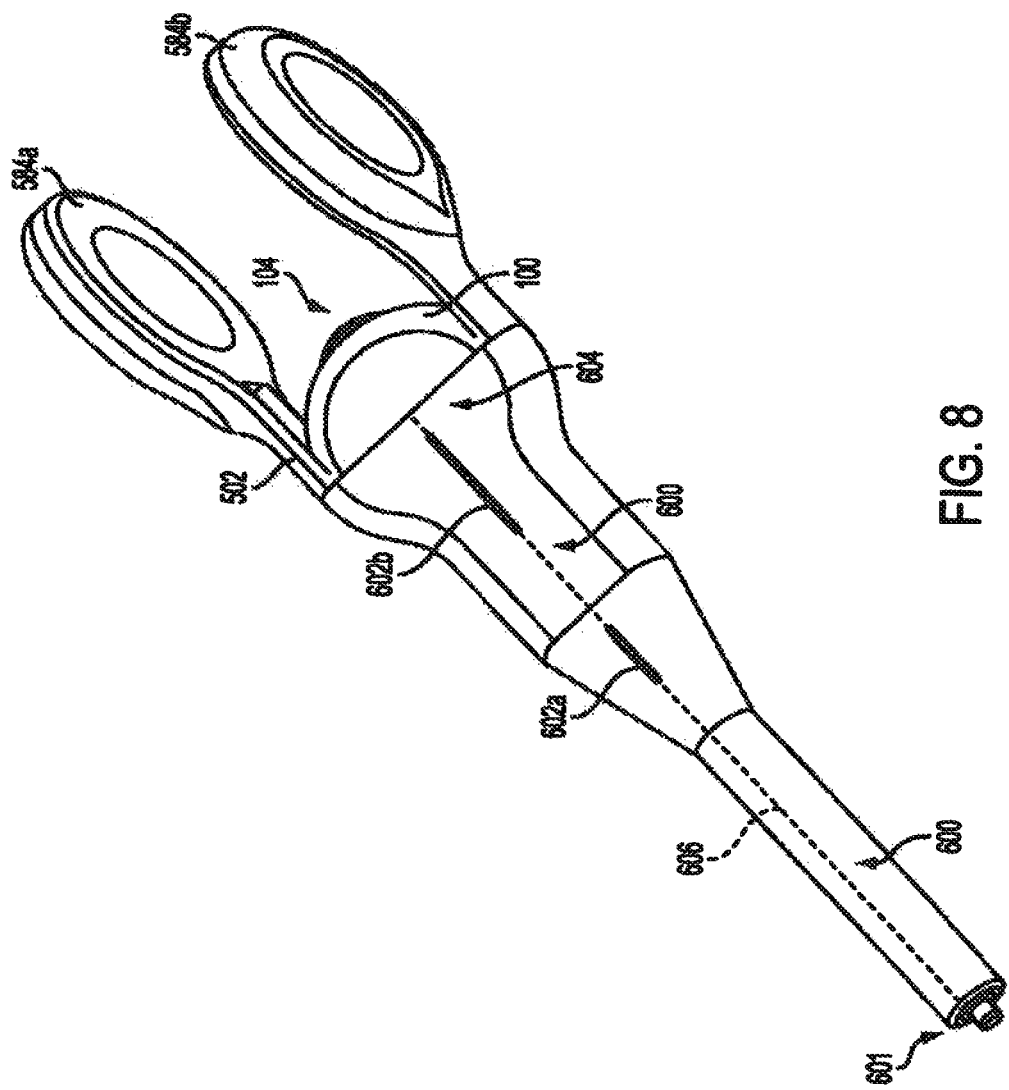
FIG. 8 is an elevation view of an exemplary implantable device positioned within an exemplary sheath.

FIG. 7 is an elevation view of an exemplary sheath, such as the sheath 502 depicted in FIG. 5. The sheath 502 includes a distal portion 580 with shape that generally matches the size and shape of a corresponding portion or portions of the implantable devices 100, 200, and semi-flexible insert 504, described above. The distal portion 580 of the sheath 502 is sized to receive the semi-flexible insert 504 within the sheath 502, as shown in FIG. 5, and to receive the implantable device 100 within the sheath 502, as shown in FIG. 8. That is, a surface of the sheath may be sized and shaped to receive the insert 504 or the device 100, as by defining a cavity that closely matches or approximates the size and shape of a least a portion of the device 100 and/or the insert 504. The sheath 502 also includes a proximal portion 582 that includes, in the depicted exemplary implementation, first and second finger loops 584 that may be grasped and pulled for sheath removal following placement of the implantable device 100, as will be described more fully below.

In various implementations, the sheath 502 may be formed of a high density polyethylene (HDPE), or of poly-tetrafluoroethene (PTFE). In some implementations, the sheath may be radiopaque. In general, the sheath 502 may be more flexible than the semi-flexible insert 504, such that when the semi-flexible insert is placed within the sheath 502 and caused to deflect, the sheath 502 may similarly deflect. The sheath 502 should nevertheless be rigid enough to hold its shape and avoid collapse when the semi-flexible insert 504 is removed following introduction of the introducer system 500 to an implant location site. That is, when the semi-flexible insert 504 is withdrawn from within the sheath 502 and removed from the body, leaving the sheath 502 at the implant site location, the sheath should generally maintain its shape without collapsing due to tissue pressure on an outside surface of the sheath.

With reference to FIG. 8, the sheath 502 may include a surface modification along an axis 600 that runs longitudinally from a distal end 601 of the sheath 502 to an area 604 of the sheath corresponding to a maximal cross-sectional width of the implantable device 100 when the device 100 is inserted within the sheath 502. Examples of such surface modifications can include perforations 606 or scoring of the sheath surface along the axis 600, notches or slits 602 along the axis 600, or reduced material thickness along the axis such that the sheath has reduced tensile strength along the axis 600. In some implementations, a first slit 602a may be positioned along the axis 600 at a position of the sheath surface corresponding to the first tapered section 120 of the implantable device 100 when the implantable device 100 is inserted within the sheath 502. Similarly, a second slit 602b may be positioned along the axis 600 at a position of the sheath surface corresponding to the second tapered section 122 of the implantable device 100 when the implantable device 100 is inserted within the sheath 502.

The surface modifications may be designed to permit the sheath 502 to split along the axis 600. For example, the modification or modifications may permit the sheath to split from the distal end 601 of the sheath to the area 604 when the finger loops 584 are pulled away from the implant site location while holding the implantable device 100 in place at the implant site location (as by applying pressure at the distal end 104 of the implantable device sufficient to prevent the device 100 from moving in response to pressure exerted on the device 100 by the sheath 502 as it is being withdrawn). When this occurs, the sheath 502 may be expected to split along the axis 600 at portions of the sheath surface corresponding to the tapered sections 120, 122 of the implantable device 100, as these are the portions where force may be concentrated on the sheath. Optionally, a second surface modification may be included along a second axis 600 on the opposite side of the sheath 502. In this fashion, force applied to the sheath at the tapered portions 120, 122 of the implantable device 100 as the sheath is withdrawn from the implant site location may cause the sheath 502 to split along the axes 600 (on opposite sides of the sheath), which may allow the sheath 502 to be pulled around the implantable device 100 and withdrawn from the body, leaving the implantable device 100 at the implant site location. Tissue trauma may be minimized during sheath withdrawal because the sheath 502 may remain substantially flat against the implantable device 100 as it is withdrawn. In various implementations, a single type of surface modification or a combinations of two or more surface modifications can be used. The modification or modifications may be along all or a portion of the axis or axes, which axis or axes may be positioned at any appropriate location along the sheath, in various implementations.

Figure 9A:
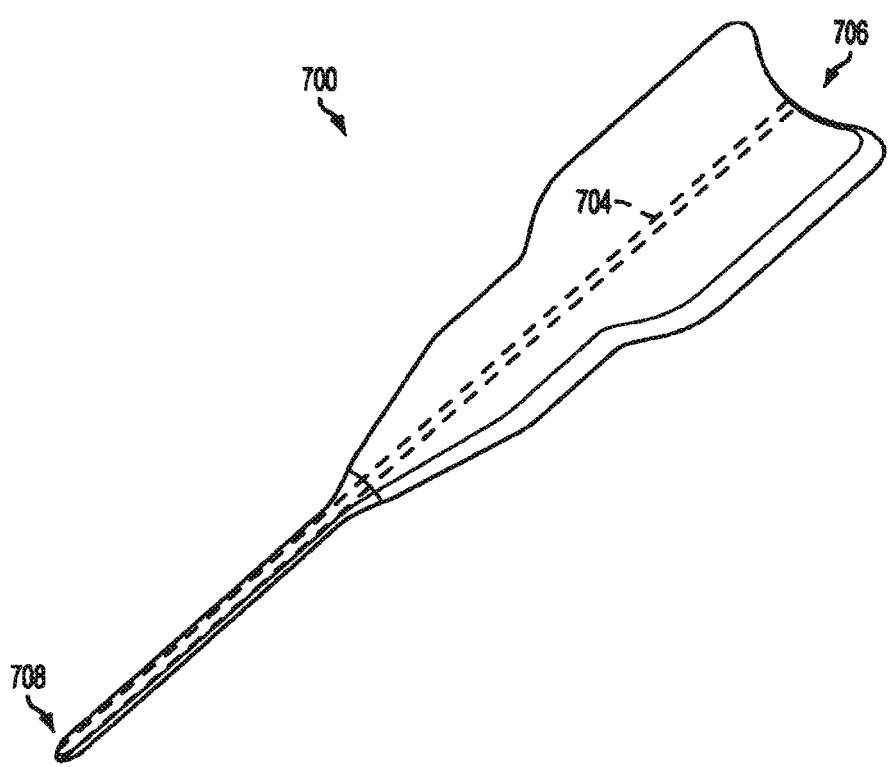
FIGS. 9A and 9B are elevation views of exemplary semi-flexible inserts that include cavities.
Figure 9B:
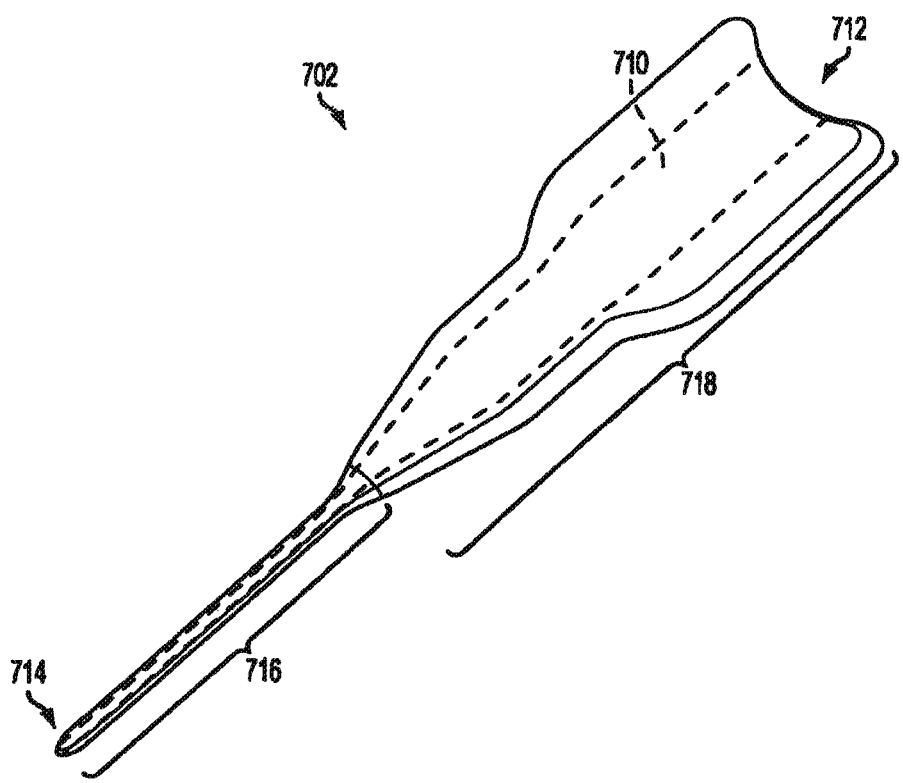

FIGS. 9A and 9S are elevation views of exemplary semi-flexible inserts 700, 702, respectively, that define cavities through a portion of the inserts. Semi-flexible insert 700 defines an isodiametric cavity 704 from a proximal end 706 of the insert 700 to near a distal end 708 of the insert 700. Semi-flexible insert 702 defines a cavity 710 from a proximal end 712 of the insert 702 to near a distal end 714 of the insert 702. The diameter of the cavity 710 may be constant for the portion of the cavity corresponding to the distal portion 716 of the insert 702. The diameter of the cavity may widen to a larger diameter, as shown in FIG. 9B, for the portion of the cavity corresponding to the mid- and proximal portions 718 of the insert 702.

Figure 10:
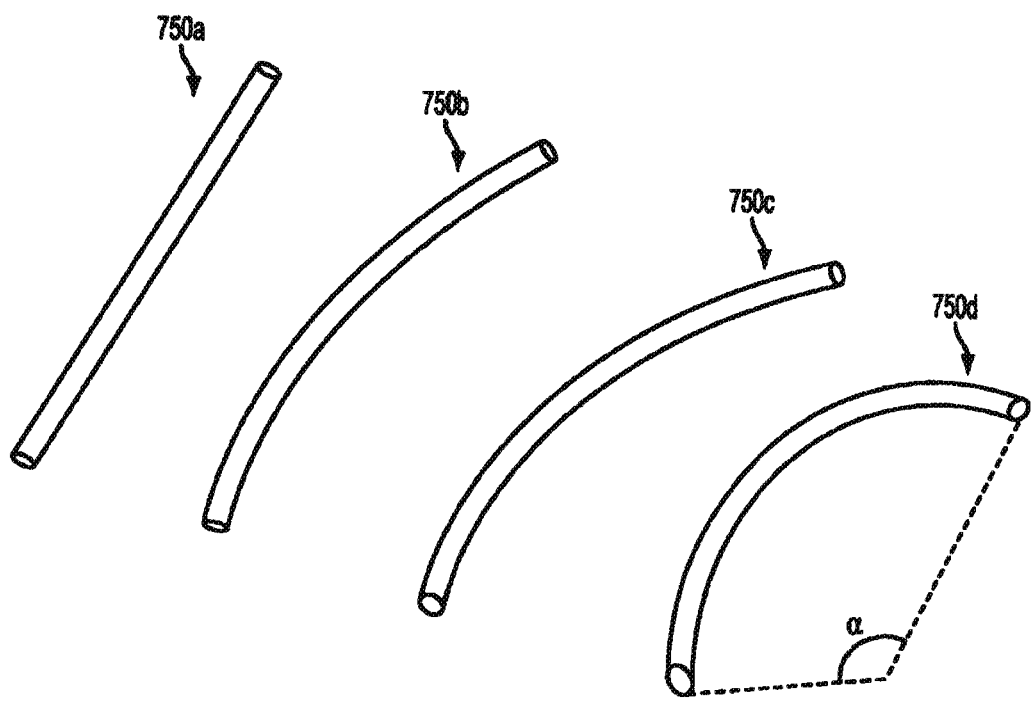
FIG. 10 is an elevation view of various exemplary insertion pins.
Figure 11:
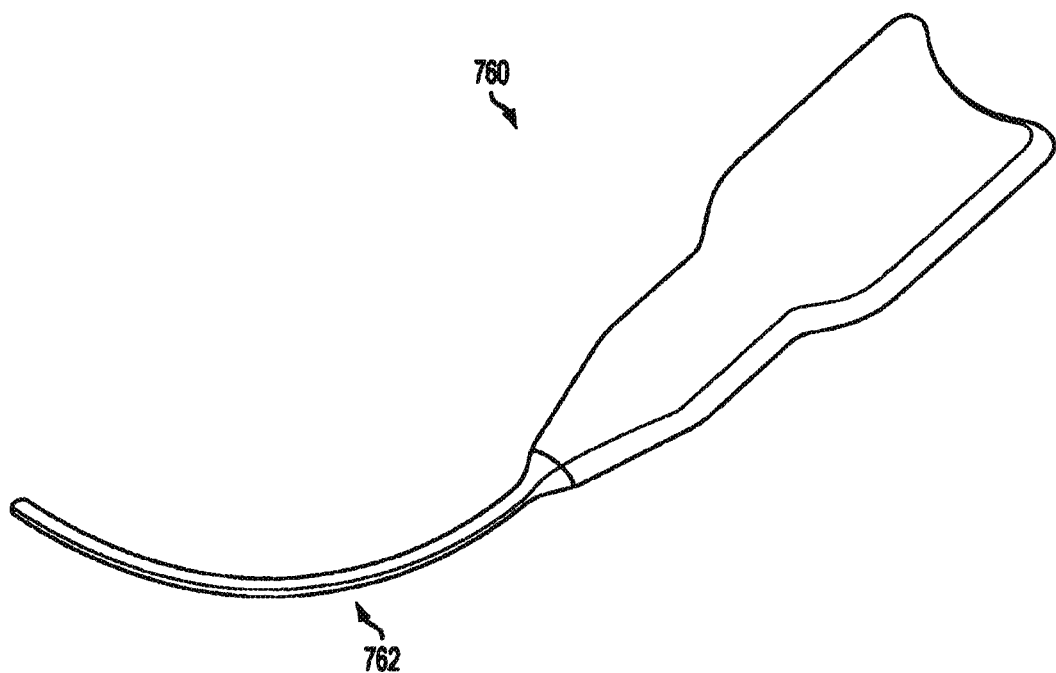
FIG. 11 is an elevation view of a semi-flexible insert with a curved distal portion.

FIG. 10 is an elevation view of various insertion pins 750 that may be inserted into the cavities 704 or 710 of the semi-flexible inserts 700 and 702, respectively. The insertion pins 750 may have constant length, and may be preformed to a particular arc angle. An insertion pin having an appropriate arc angle can be used with the introducer system discussed herein to form an implant site location pocket having a desired lead orientation for the implantable device 100. As shown in FIG. 10, insertion pin 750d has an arc angle "a." As can be seen in FIG. 10, insertion pin 750c defines a larger arc angle than does pin 750d, and insertion pin 750b defines a larger arc angle than does pin 750c. Insertion pin 750a is substantially straight, such that the arc angle that it defines is about 180 degrees. The insertion pins 750 may generally be more rigid than at least the distal portions of the semi-flexible inserts 700, 702. As such, when an insertion pin 750 is inserted into a cavity of a semi-flexible insert and pushed down into the distal portion of the insert, the distal portion of the insert may flex to assume the same arc defined by the insertion pin 750. FIG. 11 is an elevation view of a semi-flexible insert 760 with a curved distal portion 762. The distal portion 762 may be curved, for example, because an insertion pin defining an arc (such as one of the pins 750) is inserted into a cavity defined by the insert 760, as described above.

Figure 12:
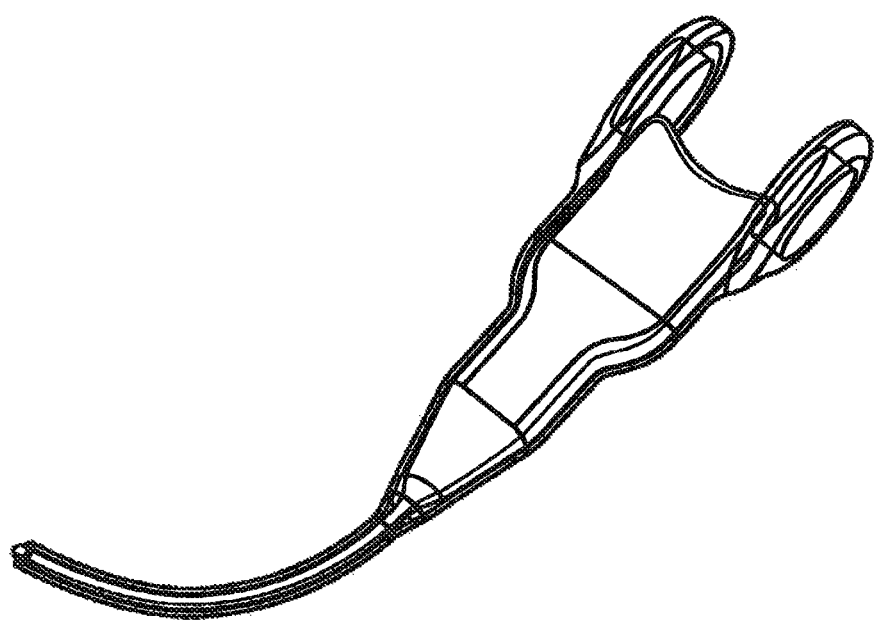
FIG. 12 is an elevation view of a sheath and a semi-flexible insert, with curved distal portions.
Figure 19:
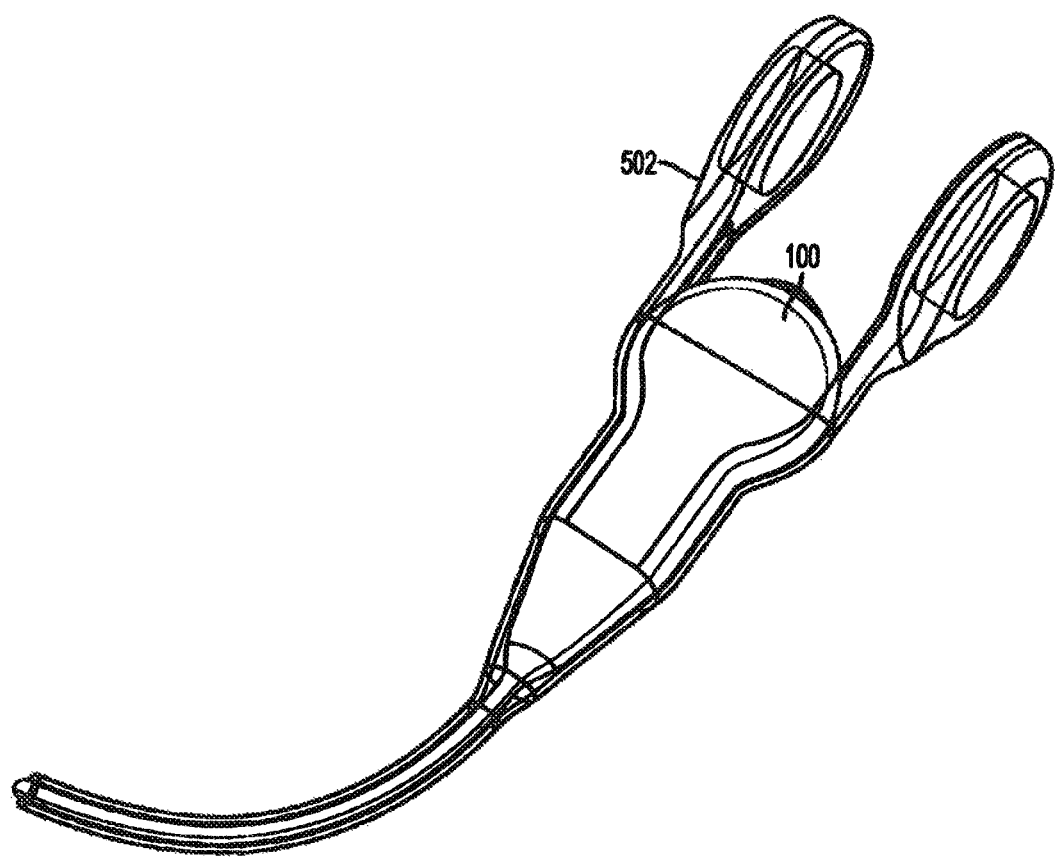
FIG. 19 is an elevation view of a sheath and an implantable device with curved distal portions.

In various implementations, the flexible insert 760 with the curved distal portion 762 may then be inserted into a sheath (e.g., sheath 502), which may cause a distal portion of the sheath to assume the curved shape of the distal portion of the insert, as shown in FIG. 12. This introducer system (here including the sheath, semi-flexible insert, and insertion pin), may then be introduced into the body of a patient to form an implant channel and implant site location. When the implantable device is then placed in the sheath following withdrawal of the semi-flexible insert, the flexible lead of the implantable device may curve at the same arc angle, as shown in FIG. 19. In this fashion, an implantable device may be implanted in a body with a curved lead orientation (for example, see FIG. 3). In various implementations, the sheath and semi-flexible insert may be partially introduced into the body initially, and then an insertion pin may be inserted into the cavity defined by the semi-flexible insert, which may cause distal portions of the insert and sheath to assume an arced orientation as described above. The sheath, semi-flexible insert, and insertion pin may then be advanced further to finish forming the implantation channel and the implantation site location with a curved lead orientation.

Figure 13:
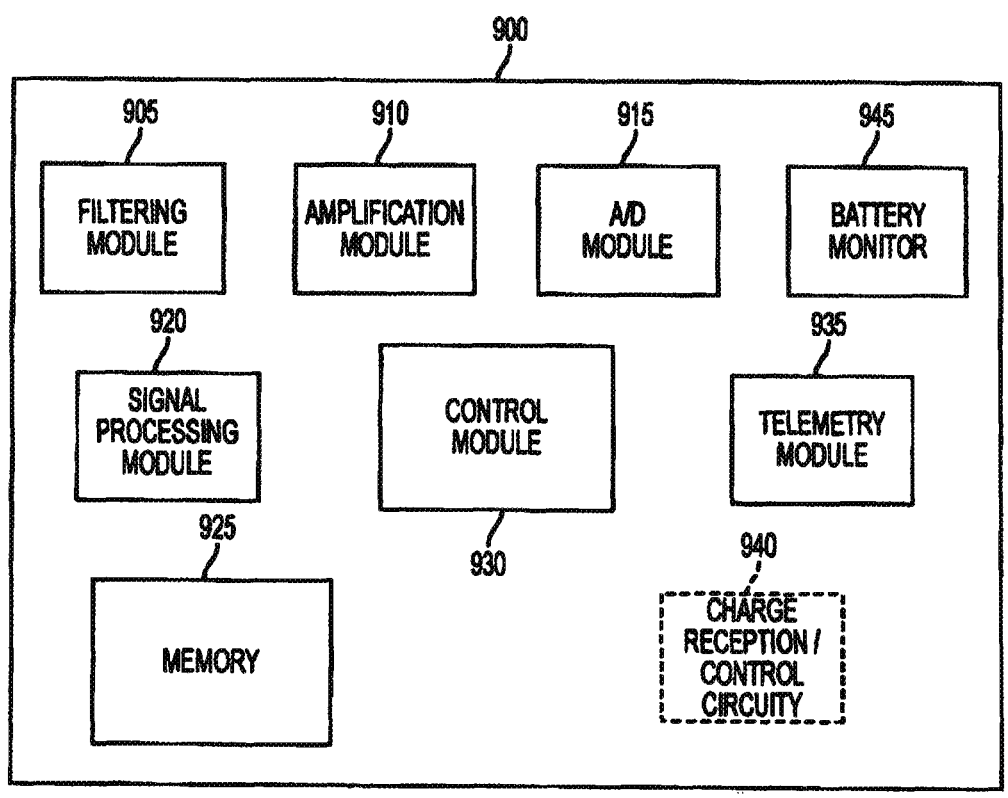
FIG. 13 is a block diagram of circuitry that may be included in implementations of the implantable device disclosed herein.

FIG. 13 is a block diagram of circuitry 900 that may be included in implementations of the implantable device disclosed herein. In some implementations, the circuitry 900 or a portion thereof may be included in the electronics module 206 shown in FIG. 4. Components or modules may be combined or separated as desired, and may be positioned in one or more portions of the implanted device. A filtering module 905 may receive a sensed physiologic signal and appropriately filter the signal to remove unwanted noise or to pare the received signal to information in a desired frequency range, or above or below a desired frequency threshold. An amplification module 910 may amplify the received signal for processing, and an analog-to-digital converter 915 may convert the analog signal to a digital signal. The digital signal may be stored directly into memory 925, or may first be processed by a signal processing module 920. Signal processing module 920 may include functions to extract information from the measured signal, or to compress the measured signal to reduce the volume of data to store and transmit. Memory 925 may include both volatile and non-volatile memory, according to various implementations, and may additionally store instructions that can be executed to perform actions. A control module 930 may provide overall device control, and may include one or more processors that can execute instructions and in response perform actions. A telemetry module 935 may be used, in conjunction with the telemetry antenna, for communication with an external device. Charge reception/control circuitry 940 may optionally be used in implementations that include a rechargeable battery to control reception of charge energy over a charge reception apparatus and coordinate recharging of the battery. A battery monitoring module 945 may provide one or more of controlling the charge current/voltage as appropriate for the type of battery, providing data that can be transmitted to a charger during charging to control and terminate charge time, assess a state of the battery from charge to depletion via voltage, impedance, charge-counting or other means, provide data to communicate to an external device for feedback as to when to charge or if an early charge is required. For simplicity, connections between the various modules are not shown in FIG. 13.

Figure 14:
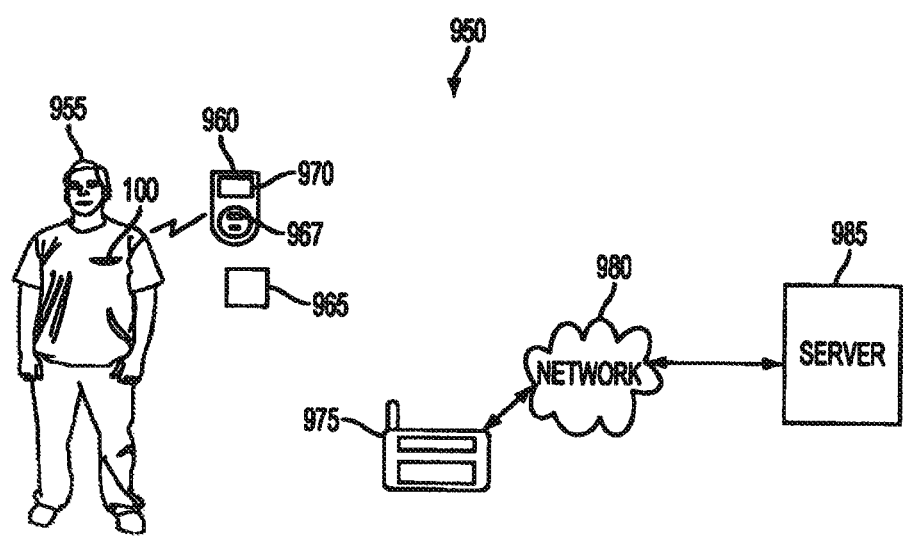
FIG. 14 is a diagram of an exemplary system.

FIG. 14 is a diagram of an exemplary system 950. The system 950 includes an implantable device 100 implanted in a body of a patient 955. The implantable device 100 may correspond to any of the implantable devices discussed herein and may be implanted according to any of the introduction techniques disclosed herein. When implanted, the device 100 may collect biological data from the patient 955. A handheld computing device 960 may be programmed to communicate wirelessly (e.g., transmit or receive data via radio frequency telemetry) with the implantable device 100. In some implementations, an external charging device 965 may be used to periodically recharge a battery of the implantable device 100, though as discussed above the device 100 may alternatively use a single-use battery in some implementations. In various implementations, the patient 955 may use the handheld device 960 to manually initiate data collection by the implanted device 100 (e.g., initiate ECG signal sensing and recording). For example, if the patient 955 feels lightheaded or feels palpitations in her chest, she may press a button 967 on the handheld device 960, and the handheld device 960 may wirelessly command the implanted device 100 to record and store physiologic data. The implanted device 100 may also record a physiologic signal when it determines that such recordation may provide useful information. For example, the device may monitor a biological parameter (e.g., heart rate), and may record an ECG signal based on predetermined characteristics of the biological parameter. In some implementations, the device 100 may periodically record sensed physiologic information according to a predetermined schedule. For example, the device may record a strip of data (e.g., covering a predetermined number of heart beats or having a predetermined strip duration or length) once every minute, every several minutes, every hour, every several hours, every day, every several days, etc.

The implanted device 100 may periodically transmit collected data to the handheld device 960, such as every few hours or once per day, for example. In some implementations, the implantable device 100 may transmit sensed data in real time to the handheld device 960, and the handheld device 960 may store the data in internal memory or display the data as a waveform or otherwise on a display screen 970 of the handheld device 960. In some implementations, functionality of the handheld device 960 and the charger 965 may be combined within a single device.

A base station 975 may communicate (e.g., wirelessly) with the handheld device 960 and/or the charger 965, and may receive data from (or send data to) either device in various implementations. The base station 975 may transmit data over a network 980 to a remote server device 985, where the data may be processed and analyzed (e.g., by a physician or a health care provider). In some implementations, data analysis may occur within the implanted device 100, the handheld device 960, the charger 965, or the base station 970. Data analysis can include detection of cardiac anomalies based on the collected data.

Referring again to FIG. 2 and FIG. 6, the distal extension 108 of the implantable device 100 may be substantially more flexible than the distal portion 552 of the semi-flexible insert 504. The flexibility of the lead 108 may permit the lead to flex with body tissue after implantation at the implant location as muscles contract and expand, for example. As described above, when the semi-flexible insert 504 of the introducer system is introduced through the layer of fatty tissue, the distal portion 552 substantially maintains direction without significant deflection through the fatty tissue, until it encounters the muscle layer. Were the implantable device 100 to instead be initially inserted within the sheath 502 and introduced to the fatty tissue layer prior to channel formation with the sheath 502 and semi-flexible insert 504, the flexible lead 108 may bend or kink, and may fail to maintain direction through the fatty tissue because of the higher flexibility of the lead 108.

A method of inserting an implantable monitoring device—which may include a rigid main body and a flexible extension collinear with a longitudinal axis of the rigid main body when unflexed—to a subcutaneous implant region of a patient may include introducing an insert device having an internal chamber that is generally in the shape of the implantable monitoring device to the subcutaneous region of the patient. The method may also include introducing the implantable monitoring device into the insert device, and removing the insert device while leaving the implantable monitoring device at the subcutaneous region. For example, the sheath 502 may be considered an insert device that includes an inner chamber generally in the shape of the implantable device.

In various implementations, any of the implantable devices, semi-flexible inserts, or sheaths, may include a single tapered section, rather than two tapered sections. In some implementations, tapered sections may be omitted.

Some implementations of the sheath. 502 may include one or more low-profile surface features on or near the distal end of the sheath to prevent the sheath 502 from moving from the implant site location when the semi-flexible insert 504 is withdrawn from the sheath 502. As one example, one or more small protrusions may provide a bit of friction when pulling backward on the sheath 502 (but not when pushing forward during introduction of the sheath and semi-flexible insert). The protrusion may be a low-profile shape having a raised portion facing the proximal end of the sheath in some implementations. For example, the protrusion may have a triangular shape, with a longest edge of the triangular shape (e.g., a hypotenuse if the triangle is a right triangle) facing the distal end of the sheath. In some examples, a corner of the triangular shape with a largest angle between adjacent sides of the triangle may be the raised portion, or the portion of the shape most-raised with respect to the sheath surface. Other shapes (e.g. diamond shape or arrowhead shape) can also be used. The surface feature or features may provide enough friction to make it easy to extract the semi-flexible insert 504 without disturbing the position of the sheath 502 at the implant site location, but not enough to cause tissue abrasion when extracting the sheath after placement of the implantable device. In some implementations, the surface feature(s) may be omitted. While withdrawing the insert 504, the physician may apply a force to the sheath 502 to prevent the sheath 502 from moving as the semi-flexible insert 504 is withdrawn, for example.

Exemplary widths of the implantable devices discussed herein may be, at their widest point, about 17.8 mm in one implementation and about 22.1 mm in an alternative implementation, though even smaller widths are possible. With devices having these widths, skin incisions as narrow as 13.5 mm or 17 mm may be possible.

In some implementations, the implantable device 100 may be subcutaneously implanted without using the introducer system. For example, a physician may use a hemostat tool to grab, for example, the distal tip of the flexible extension 108, and use the hemostat to insert the device under the skin. The one or more tapered sections of the implant device 100 may facilitate the insertion, in this example.

In an implementation, the device is implanted such that the rigid body of the device occupies an upper-pectoral-region subcutaneous position, and the flexible lead is routed inferiorly and located over a right atrium of the patient. For example, a distal end of the lead may be positioned near a middle of the lower chest, over the sternum.

Figure 21:
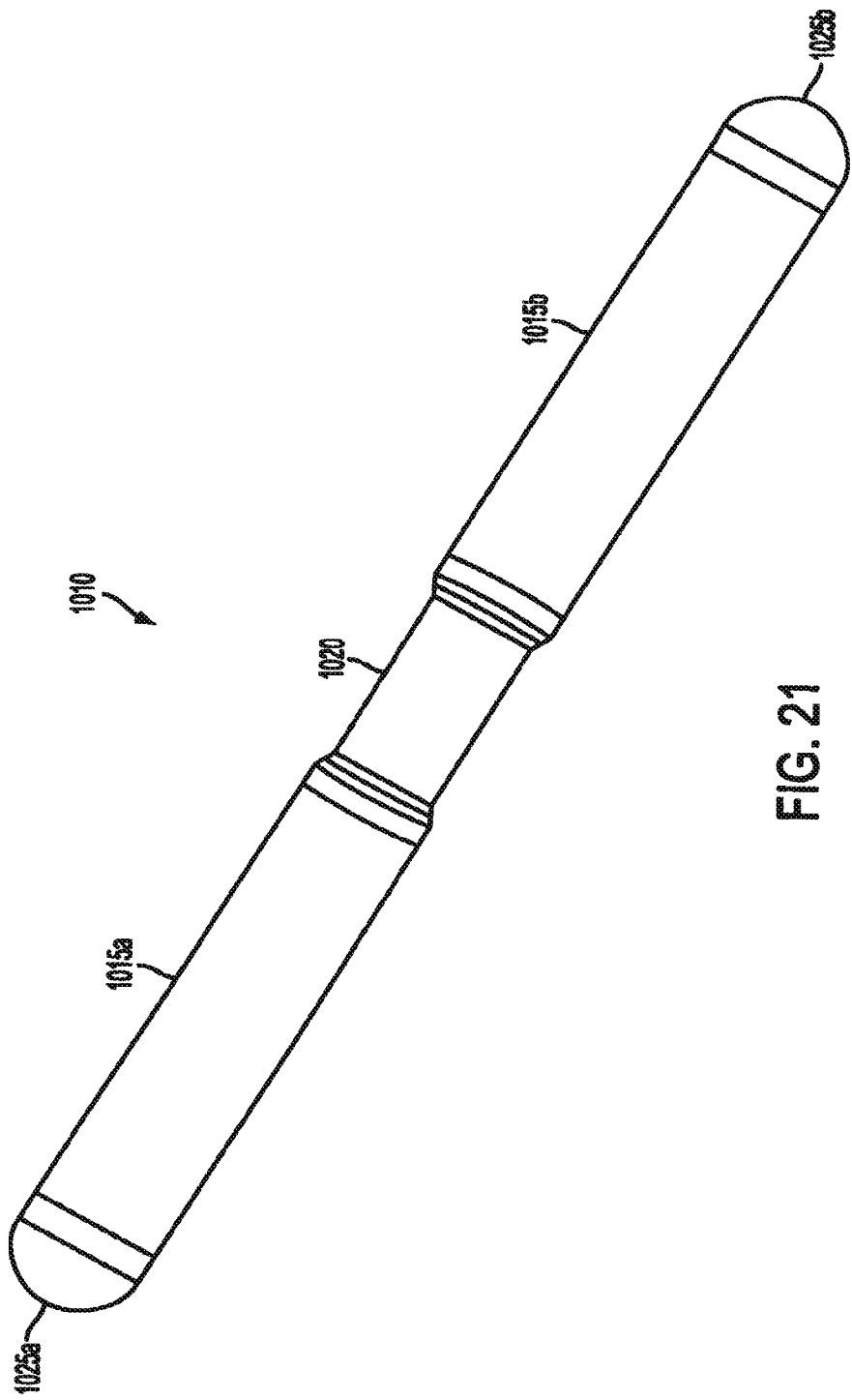
Figure 22:
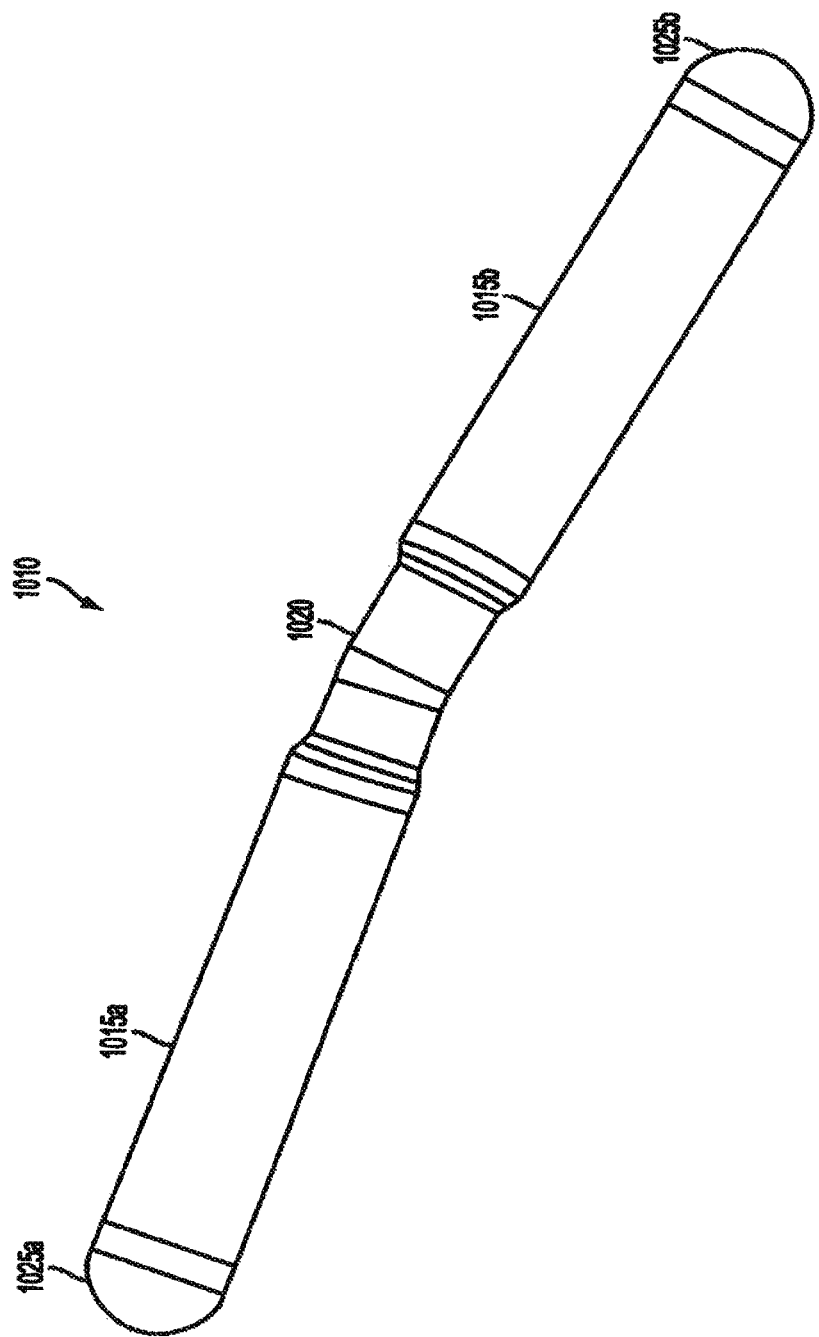

FIGS. 21-22 are exterior views of an alternative exemplary implantable device 1010 that includes at least two rigid sections 1015 separated by at least one flexible section 1020. As shown in FIG. 22, the flexible section 1020 may flex or bend at an appropriate angle, which may permit the implantable device 1010 to better fit contour of a body following implantation in the body of a patient, as the device 1010 may conform to body tissue at the implant location and flex with movement of the surrounding tissue. This may provide increased comfort for the patient, and may permit improved functionality of the device, as will be explained more fully below. The device 1010 may include the functionality of the implantable devices discussed above, according to some implementations.

In some implementations, the device 1010 may be relatively small, and may be sized and shaped for convenient implantation within a body of a patient, such as at a subcutaneous implant site, for example, in a pectoral region of a human patient. For example, the device 1010 may be generally cylindrical in shape (having a round cross-section) and may have a length within the range of about 4 cm to about 10 cm, an outside diameter in the range of about 4 mm to about 10 mm, and may be inserted or injected under the skin of a patient using a trocar or similar insertion device, according to some implementations. A round cross-sectional shape may provide compatibility with existing round-bore trocars or other surgical tools. This implant method may result in only a small, minimum-trauma entry point in the skin and a tunnel for the device, which may facilitate clean tissue healing that results in a less noticeable scar at the implant site as compared to conventional implantation procedures for larger devices.

FIG. 21 shows one example of an implantable device that has an overall shape that is elongate and generally tubular, with the longitudinal ends rounded. The example implantable device of FIG. 21 is made up of two in-line, rigid, elongate tubular sections. A flexible portion connects the two rigid, elongate tubular sections, and allows the rigid sections to move (for example, bend) relative to one another. In addition, the device includes two electrodes, namely, a first electrode on a first longitudinal end of the device, and a second electrode on a second longitudinal end of the device. The electrodes are rounded.

As shown in FIG. 21, the device 1010 is in a substantially straight orientation, where the flexible section 1020 is not bent at an angle. The device 1010 may be placed in the trocar with this orientation for injection into the patient. Upon delivery to the implant location, the flexible section 1020 may bend to conform to surrounding tissue at the implant location, and thereafter may flex in response to patient movement throughout the period of implantation. In various implementations, the flexible section 1020 may flex or bend in the longitudinal direction, in the transverse direction, or in both the longitudinal and the transverse directions. As an alternative implantation method, a physician may make a small insertion in the patient's skin, and may form a subcutaneous tunnel to receive the device.

In the example depicted in FIGS. 21-22, electrodes 1025 are positioned at the longitudinal ends of the device 1010. The electrodes 1025 in the example implementation are hemispherical in shape and are at longitudinal ends of the device, although they may take any appropriate shape (e.g., button, ring, etc.) and may be placed at any appropriate location on the device. The depicted example includes two electrodes 1025a, 1025b, but other implementations can include more electrodes (e.g., 3, 4, 5, 6, etc.), which may be used in various implementations as sense electrodes and/or as stimulation electrodes. The electrodes 1025a and 1025b are on the body of the device 1010, and are each near a longitudinal end of the device 1010. This placement may maximize signal vector length of a measured physiologic signal. The length of the device 1010 may be varied depending upon its construction and upon a desired ECG signal amplitude. For example, in implementations where the device 1010 monitors an ECG signal from a subcutaneous pectoral implant location, measured amplitude of a detected R-wave may be about 10 uV per 1 cm of electrode separation distance. Positioning the electrodes 1025a, 1025b near opposite ends of the device 1010 may maximize the amplitude of the sensed physiologic signal for a given device length, which may lead to better measurement results.

Figure 23:
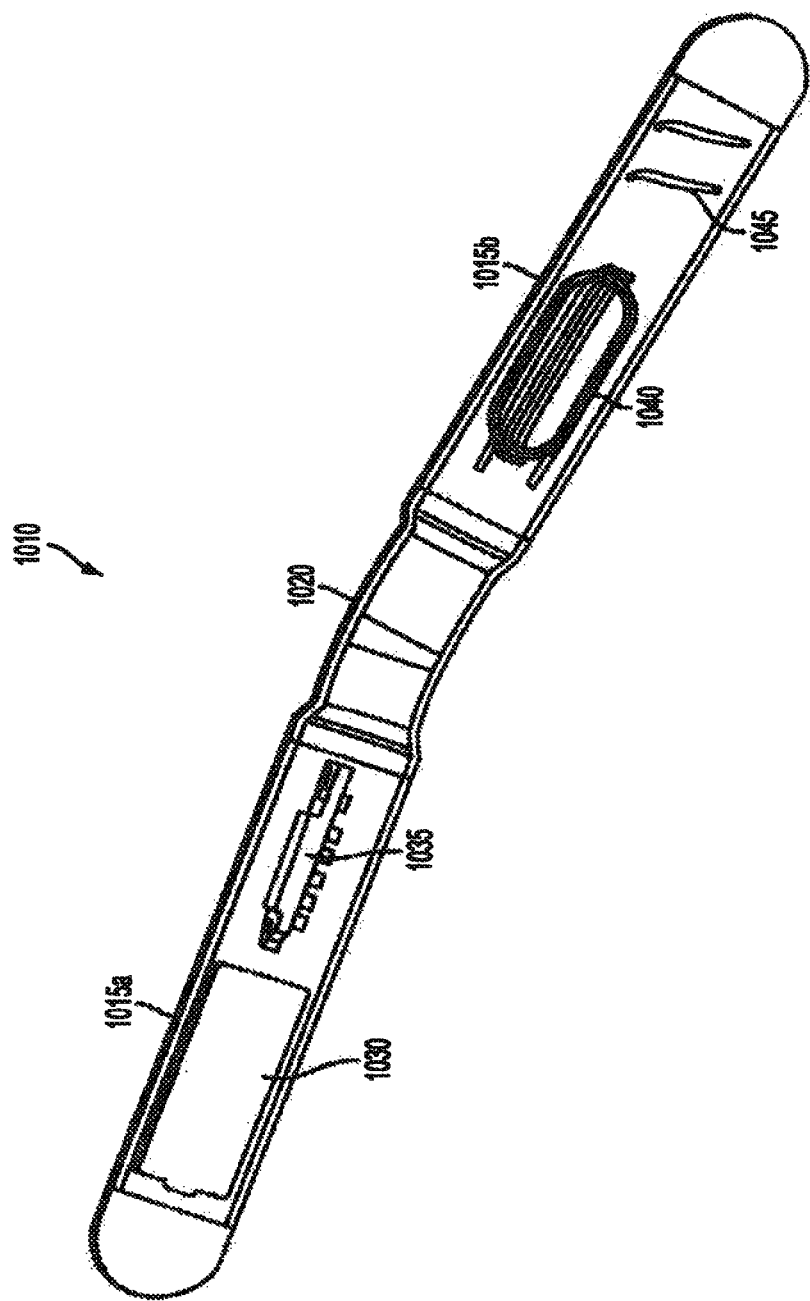
FIG. 23 is a view of the exemplary implantable device of FIGS. 21-22, showing selected components housed within the device.

In some implementations, the rigid sections 1015 may be hermetically sealed and the flexible sections 1020 may be non-hermetic. In other implementations, some of the rigid sections 1015 may be hermetic and others may be non-hermetic. In various implementations, exterior surfaces of the hermetic sections may be fabricated from a metal or ceramic, and exterior surfaces of the non-hermetic sections may be fabricated from a polymer. In some implementations, the flexible sections 1020 may be of reduced diameter compared to the rigid sections 1015 for improved flexibility, as shown in FIGS. 21-23. In other implementations, the flexible sections 1020 may be of diameters similar to those of the rigid sections 1015, such that, at the end of its useful life, the device may be more easily extracted from the patient.

An exterior surface of the rigid sections 1015 may be fabricated of a metal such as titanium, according to some implementations. An exterior surface or a portion of an exterior surface of a rigid section may be used as an electrode (e.g., as a sense or stimulation electrode). Rigid segments not used as an electrode may be coated with an insulator (e.g., parylene), which may avoid formation of conductive paths across the device sensed parameter vector. If a portion of the rigid section 1015 is to be used as an electrode, the remaining portion may be coated with an insulator.

The rigid sections 1015 may house electronics and components that permit the implantable device 1010 to function.

FIG. 23 shows the device 1010 with a battery 1030, an electronics module 1035, a charging apparatus/coil 1040 and a telemetry antenna 1045 disposed within the rigid sections 1015 of the device 1010. In this implementation, the battery 1030 and electronics module 1035 are grouped within the first rigid section 1015a, and the charging coil 1040 and the telemetry antenna 1045 are grouped within the second rigid section 1015b. Section 1015a may be hermetic to protect the electronic components from water vapor ingress. Section 1015b may be non-hermetic to allow the use of enclosure materials that are non-conductive and will not attenuate the electromagnetic signals transmitted or received by the enclosed components. The flexible section 1020 separates the rigid sections 1015, and permits the device 1010 to flex and conform to surrounding tissue at the implant location. This may permit the device to both stretch and flex to maintain high-quality electrode contact during body movement.

The rigid sections 1015 can be sized so that they are small enough to avoid causing skin irritation or discomfort for the patient, yet large enough to hold the electronics or components that permit the implantable device to function. In some implementations, the rigid sections are less than about 3 cm in length. The sizes of various sections of the device may be varied with respect to other sections, whether by length, width, or shape. For example, rigid sections may be sized according to the components or circuitry they will house.

Figure 25:
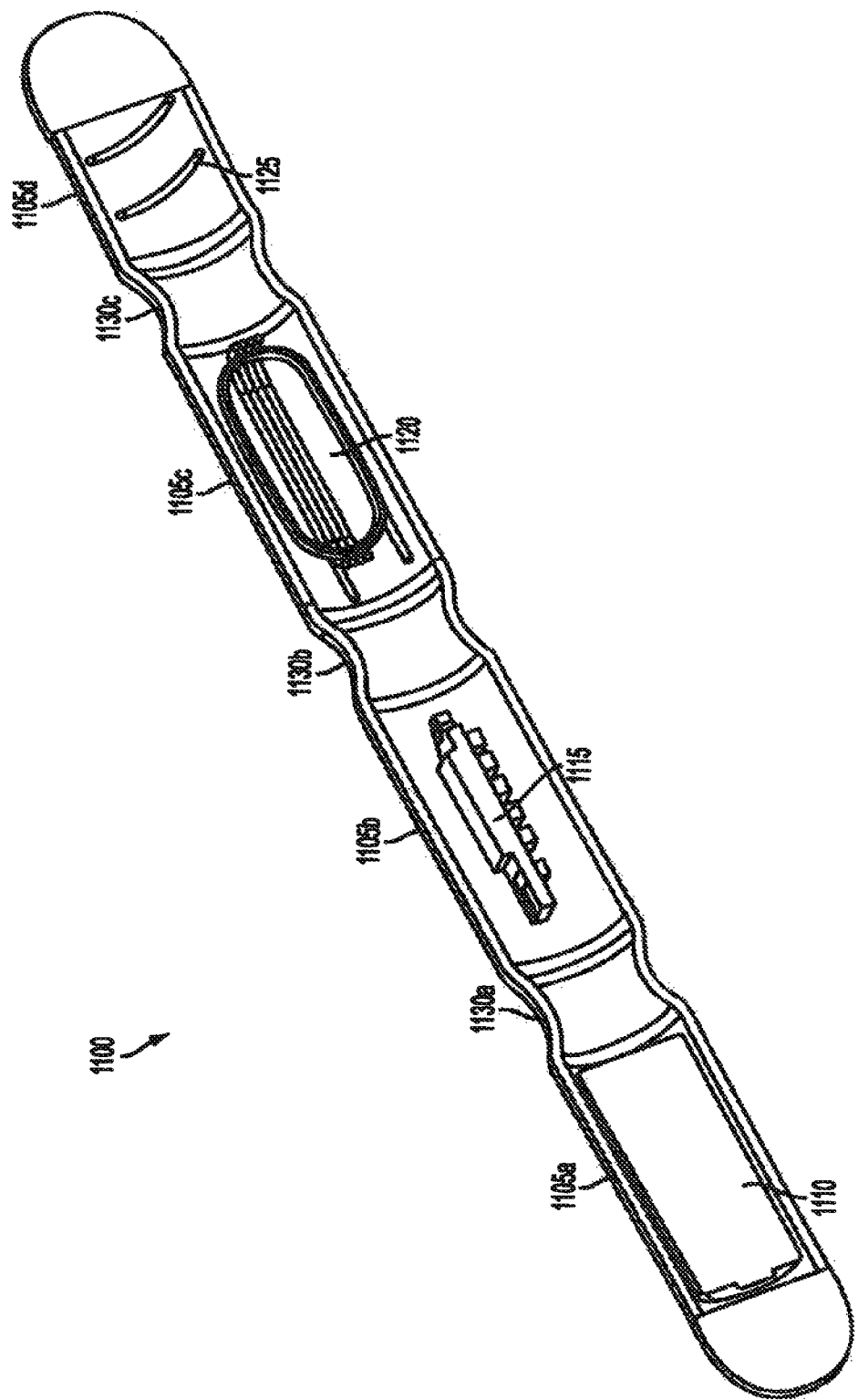
FIGS. 25-26 are views of exemplary implantable devices showing selected components housed within the devices.

FIG. 25 shows a device 1100 that has four rigid sections 1105. A first rigid section 1105a houses a battery 1110; a second rigid section 1105b houses one or more electronic modules 1115; a third rigid section 1105c houses a charge reception mechanism 1120, and a fourth rigid section 1105d houses a telemetry antenna or coil 1125. As shown in FIG. 25, the rigid sections 1105 have varying sizes as appropriate. Flexible sections 1130 separate adjacent rigid sections, and permit the device 1100 to flex to conform to body tissue at an implant location, in similar fashion as described above with respect to device 1010. The three flexible sections (1130a, 1130b, 1130c) may flex independently, each bending an appropriate angle and an appropriate direction to conform to a tissue contour at the implant location. In various implementations, any number of rigid sections 1105 or flexible sections 1130 may be used. In implementations that include at least two flexible sections 1130, the flexible sections may bend such that the device assumes a three-dimensional orientation, rather than a planar orientation (e.g., as with a single flexible section permitting bending in a single direction), or a linear orientation (e.g., as with a rigid, straight device).

In various implementations, the components of the device can partitioned between rigid segments in a manner that minimizes the number of interconnects between segments. In one exemplary implementation (not shown), three rigid segments of length 2.5 cm house a battery, electronic circuitry for ECG measurement and telemetry, and a recharging apparatus/coil and telemetry antennae, respectively. The segment with the recharging apparatus/coil and telemetry antennae may be molded with a polymer such as urethane to avoid having a conductive housing that could attenuate the power or telemetry signals.

The flexible interconnect sections (1020, 1130) may take many different forms. Material choices for the flexible sections may include elastomers such as silicone or polyurethane. The elastomer section may have a sleeve of wire braid or mesh embedded, which may add strength or may prohibit flexure beyond a predetermined angle. Since the elastomer materials are non-hermetic, hermetic feedthroughs (not shown in the figures) may be provided where electrical connections enter/exit the hermetic sections to maintain hermeticity of that section. Electrical connections through the interconnecting element may take the form of a helix, which may provide a long flex life. The electrical conductors may be molded into the elastomer material to minimize or prevent voids where water may accumulate. The electrical connections may optionally be coated with parylene or other material to provide a secondary formfitting barrier that isolates each conductor. In some implementations, the helical conductors and elastomer may each contribute stiffness to the flexible section that, in combination, may permit bending sufficient to move with body flexure but resist extreme bending due to device migration or manipulation by the patient. Where there are adjacent hermetic segments, the hermetic feedthroughs for the mating ends of the segments may be sourced as a single assembly, including contiguous conductors through and between them. This may reduce cost and provide increased robustness for the device.

Referring again to FIG. 23, the device 1010 may use a rechargeable battery 1030 and an associated charging mechanism 1040 to extend operational life of the device 1010. Because the device has relatively small size, and because the device may be implanted in a patient for a period of several years, a rechargeable battery may provide a convenient alternative to extracting the device and replacing an expired battery. The battery 1030 can be recharged via magnetic field transmission of energy from outside the body. One or more coils 1040 in the device 1010 may closely couple to one or more coils in a charging apparatus external to the body. The external charging apparatus may take various forms, as will be discussed later, but in general the external charging apparatus may be positioned in relatively close proximity to the implanted device location to facilitate efficient charging. Possible choices for the charging frequency may include 125 KHz, 6.78 MHz (ISM), and 13.58 MHz (ISM), where ISM indicates frequency bands allowed by the FCC for use by Industrial, Scientific, and Medical equipment that uses RF (radio frequency) energy but not for the purpose of telecommunication. Energy at these frequencies may be largely transferred by magnetic field, as the implant will be close enough to be in the "near-field" of the charger. For patient convenience and to maintain close contact between charger and implant, the charger can be patient-worn and battery powered. In some implementations, the external charger can be incorporated in a wearable clothing item or accessory that is unobtrusive yet holds the two devices in close alignment for optimal coupling. The battery need not be rechargeable in some implementations, and in these cases the recharging coil 1040 may be omitted.

Recharging may alternatively be accomplished via ultrasound energy, light energy, or radio frequency energy originating from outside the body. In an implementation, energy generated by movement (motion or flexure), chemicals, or temperature differentials within the body is used to recharge the battery 1030. Energy from body motion may be harvested within the device 1010 by components that convert motion to force/displacement (e.g. via inertial forces on a weight), and force/displacement to electrical energy (via a material such as a piezoelectric material), as will be discussed more fully below. Energy derived from body flexure (resulting in device flexure) may only require conversion of force to electrical energy.

Figure 24:
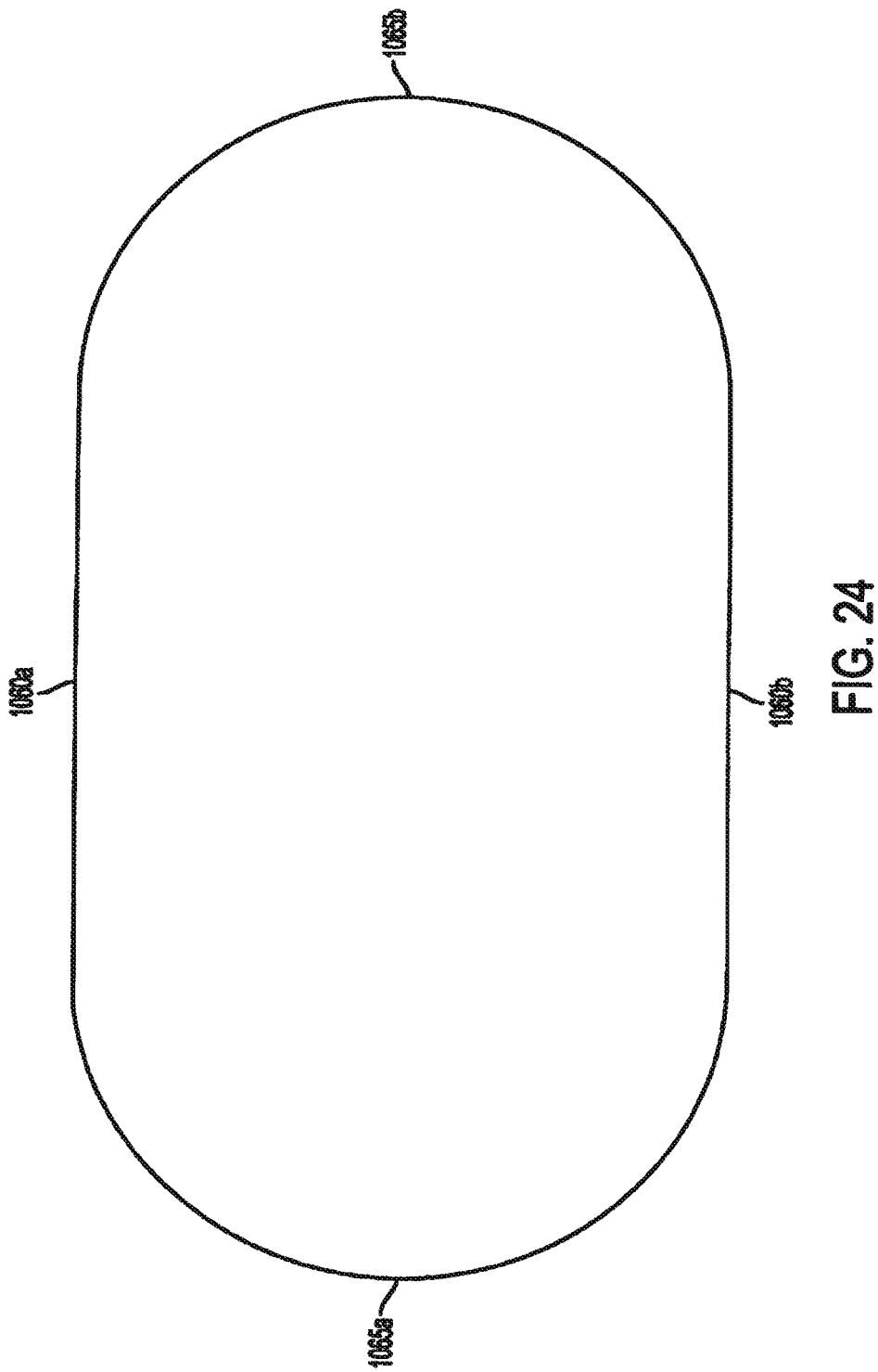
FIG. 24 is a cross-sectional view of an exemplary implantable device having a flattened cross-sectional shape.

Device cross-sectional shapes other than circular may be used. FIG. 24 shows a cross-sectional view of a device implementation having a flattened cross-sectional shape. The flattened cross section has opposing relatively flat major sides 1060 and opposing rounded minor sides 1065. This implementation provides a flatter cross-section, which may readily accommodate electronic circuits and components that have flat construction, such as circuit boards and components or integrated circuits that attach thereto, for example. Such a shape may also be more conducive to physiologic measurements, in that the device may be less likely to rotate about its longitudinal axis. The flatter shape, because it may minimize or prevent device rotation, may also permit better measurement results as electrode surfaces may move less with respect to contacting tissue. As such, a preferred orientation established at implantation time may be maintained. Minimizing or preventing device rotation and providing fixed and predictable orientation of a flat side 1060 to the skin surface may provide an advantage where internal telemetry or power reception coils have an axis perpendicular to the long axis of the device. Such an orientation may help to overcome challenges related to an implant that has migrated or rotated to create an uncontrolled orientation between the external charger and implanted device coils, as such misalignment may greatly decrease the rate at which the battery 1030 is charged.

A device with such a shape could be injected with a trocar that has a deformable bore or is preformed with a matching flattened bore. A trocar with a round bore can be used to place an initially round but flexible sheath that can then flex to insert the device with ovoid cross section through it after the trocar is removed. Alternatively, a trocar with a round bore sized to accommodate the flattened cross section of the device could be used to inject the device without the sheath.

While harvesting energy from body flexure for powering electrical circuitry or charging a battery may be used with any of the implementations described herein, it may be particularly appropriate for implementations that include multiple rigid hermetically sealed segments and flexible segments that interconnect them. When such body movement occurs, forces from body flexure are applied to the rigid segments, and then concentrated at the flexible interconnecting elements. One or more piezoelectric elements may be incorporated within the flexible segment (s) (or within a flexible extension), which may flex in response to the body movement and movement of the rigid segments relative to each other. The one or more piezoelectric elements may then generate electrical energy as a result of the movement. Such flexure may arise, for example, from a continuing repetitive body function such as respiration, or intermittent voluntary flexure initiated by skeletal, muscles.

Some implementations include a liquid enclosed within one or more flexible sections. The liquid can be used to accumulate the force applied to the flexible joint, as described above, and refer that force to the piezoelectric element for generation of electrical energy that may be used to power electrical circuitry or charge a battery of the device. A space defined by the flexible section may be designed to deform with joint flexure such that volume and/or pressure of the liquid changes in response to flexure of the joint. The piezoelectric element can be coupled to the space enclosing the liquid such that changes in liquid pressure deform the piezoelectric element and cause electrical energy to be generated. In some implementations, the space may be defined by a void within an elastomer such that extreme pressure changes are limited by compliance of the elastomer and do not rise to levels that would damage the piezoelectric element. In various implementations, the piezoelectric element may be mounted on a diaphragm to provide structural integrity and media isolation from the liquid. The liquid may be chosen to have a chemical composition that minimizes permeation through the elastomer over time, and may be biocompatible so that any fluid that is leaked to surrounding tissue has benign effect. Alternatively, the space containing the liquid may be defined by a metallic structure. The metallic structure may incorporate a bellows-like feature to improve flex life and provide compliance to limit pressure. This implementation may eliminate the need to choose the liquid based on permeability considerations.

Figure 26:
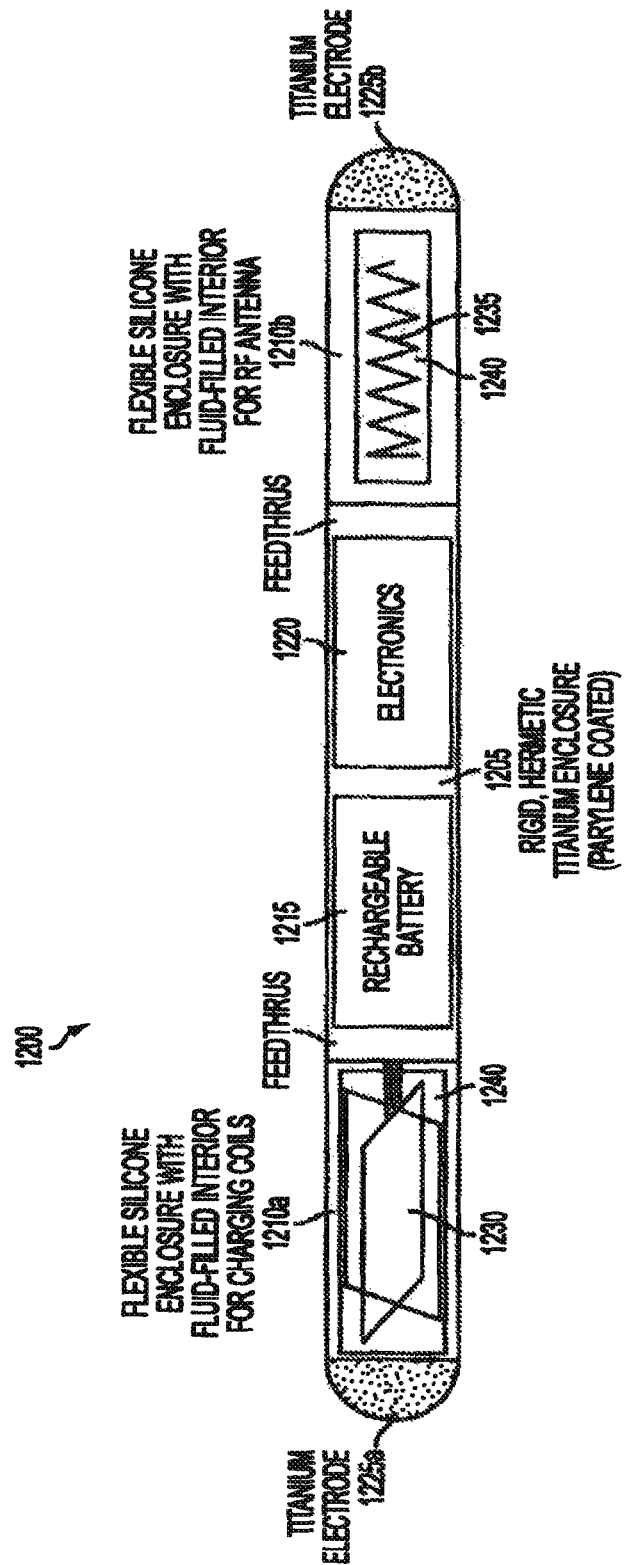

FIG. 26 shows an implementation of a device 1200 that includes a rigid center section 1205 and two flexible sections 1210, each connected to the rigid section 1205. In this implementation, the rigid section 1205 is hermetic and houses a battery 1215 and electronics 1220 that control operation of the device 1200. The flexible sections 1210 may be relatively short, flexible, stretchable extensions of the center section 1205. First and second electrodes 1225*a* and 1225*b* (e.g., sense electrodes or stimulation electrodes, or a combination) are attached, respectively, to the flexible sections 1210*a* and 1210*b*, and may facilitate high-quality electrode-tissue contact. The electrodes may be composed of titanium in some implementations.

In some implementations, the flexible sections or extensions 1210 may be comprised of silicone. The flexible extensions 1210 may be designed to also enclose or embed components suited for housing in a non-conductive enclosure, such as components that communicate by field or wave properties. In the depicted example, the leftmost extension. 1210*a* encloses a recharging coil 1230 and the rightmost extension 1210*b* encloses a telemetry antenna 1235. An embedded recharging coil or telemetry antenna may be designed with a wire-type and/or geometric construction that would allow the component to flex with the flexible extension in response to a contour or movement of surrounding tissue material without sacrificing long-term reliability. Alternatively, these components 1230, 1235 may be of a rigid construction, which may allow a wider selection of appropriate wire types and geometric constructions.

A rigid component construction may be more resistant to long-term flexure failure, and may provide greater stability of electrical properties of the component, such as resonant frequency. In the case of rigid construction, the component 1230, 1235 may be enclosed or float within a fluid-filled cavity defined by the extension 1210, which may minimize or eliminate shear stresses associated with direct adhesion of the silicone to the component 1230, 1235. FIG. 26 shows a fluid 1240 encapsulating the charging coil 1230 and the telemetry antenna 1235 within cavities defined by their respective extensions 1210*a*, 1210*b*. Component encapsulation with fluid may also allow the silicone extension 1210 to retain a higher degree of flexibility. The fluid used to fill the cavity can be chosen to avoid loss by permeation through the flexible material, such as a perfluorocarbon for a silicone extension 1210. Materials and geometries for conductive connections to the electrical components (e.g., recharging coil, telemetry antenna, or sensing electrode) may be chosen to allow repeated flexure without failure. In one implementation, an MP35-N Stainless material and a helical geometry are used.

Another implementation includes, as an alternative to an electrode on the body of the device (e.g., as shown in FIGS. 21-23 and 25) or on a short flexible extension (e.g., as shown in FIG. 26), one or more electrodes incorporated on one or more longer, flexible leads constructed much like a short pacemaker lead. This approach may provide for a possibility of higher amplitudes of sensed EGG signals due to a longer sense vector, and may provide a more stable electrode placement. In some implementations, the lead or leads may be formed integral with the body of the device, such that no connectors would be needed. Some implementations include one electrode attached to one end of the body of the device, and a single lead with attached electrode extending from the opposite end of the device. Extraction of such a device may involve pulling the device from the lead, and in these implementations a sufficiently high tensile strength of the lead may be specified. In some implementations, the flexible EGG sensing lead also performs the role of the telemetry antenna through the use of the conductor connecting to the EGG electrode or a separate conductor. In some implementations, the telemetry antenna function is incorporated in a flexible lead independent from any EGG sensing lead. In general, features of any of the implantable devices discussed herein may be combined or separated as appropriate.

Figure 27:
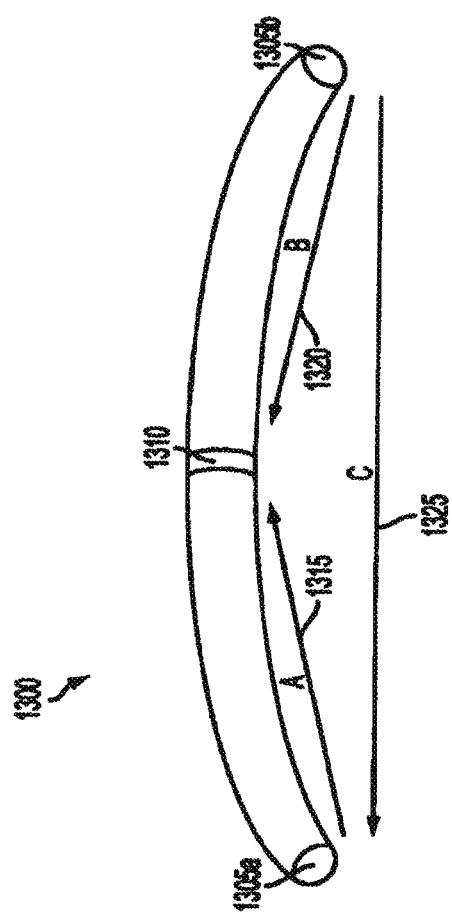
FIG. 27 is an exterior view of an exemplary implantable device that includes three electrodes.

FIG. 27 shows an exterior view of an exemplary implementation of a device 1300 that includes three electrodes. First and second electrodes 1305 are positioned on the body of the device at opposing ends of the device, in similar fashion to some of the embodiments discussed above. Additionally, a third electrode 1310, shown illustratively as a circumferential or ring electrode near the center of the device, is provided. With three electrodes as shown, the device 1300 may measure any of three different physiologic signal vectors: a first vector 1315 (labeled "A") between the leftmost end electrode 1305*a* and the middle electrode 1310; a second vector 1320 (labeled "B") between the rightmost end electrode 1305*b* and the middle electrode 1310; and a third vector 1325 (labeled "0") between end electrodes 1305*a*, 1305*h*. The device 1300 is curved to adapt to a tissue implant location, according to some implementations. In some implementations, the device 1300 is a rigid device, while in other implementations one or more sections of the device 1300 may be flexible. Such a device may be inserted under the skin via a curved trocar or sheath, according to some implementations. The device 1300 may have a circular or flattened cross-sectional shape. The device 1300 may include more or fewer electrodes. Implementations that include additional electrodes would be able to measure additional physiologic signal vectors, which may provide a more global assessment of the physiologic signal and associated body function. Any of the electrodes 1305, 1310 may have any appropriate shape, including a button electrode on a particular side of the device.

One implementation of a rigid device, such as the device 1300 shown in FIG. 27, may be implanted between ribs of a patient. Such a location may provide protection for the device and minimize tissue pinching. For example, an inframammary approach, such as disposing the device between ribs 4 and 5 or between ribs 5 and 6, may provide a suitable location for sensing a high-quality ECG signal, and leave the device less exposed and less subject to movement or impact. Device reliability may be improved as a result. The device may include any appropriate number of electrodes, and may be sized and formed appropriately for the target patient.

As described above, charging energy may be provided to the implantable device in a number of ways, and the device may include a component or circuitry to interface with the external charging unit. For device implementations that utilize magnetic-field recharging means, the device may include a coil (e.g., coil 1040, 1120, or 1230) for receiving charge energy that is as large as practical to maximize the energy transfer rate. In some implementations, the coil is not be shielded by a conductive housing. At charge frequencies of about 125 KHz, however, attenuation through a conductive housing may be low enough to still allow feasibility. In implementations where avoiding coil enclosure within a conductive housing is desirable, the coil may be incorporated in one or more of the flexible segments. Alternatively, housing enclosing the charge reception coil may be ceramic, which can be hermetic yet still pass the magnetic field energy with minimal attenuation. Implementations that include multiple flexible segments can have coils in multiple segments to improve reception of charge energy and reduce charge times or increase a distance within which the external charge device must be maintained with respect to the implanted device during charging.

Some implementations include multiple coils arranged in different orientations within a single segment. For example, FIGS. 23 and 25 show charge reception apparatuses 1040, 1120 having coils arranged in orthogonal orientations. When multiple coils are used, their output may be summed, or the highest output coil may be selected via active or passive means. Coils whose axis is aligned with the long axis of the implant may be able to flex with the joint, as the helix formed by the turns of the coil may form a spring. Use of ferrite cores within coils may enhance coil ability to receive energy, but may reduce flexure of the coil and add weight to the device, and may create magnetic force on the device during an MRI procedure. In another implementation, a rigid segment contains a charge reception apparatus (e.g., one or more coils) and is molded with a polymer, such as urethane, with the polymer body forming the outline of the rigid segment.

Alignment of the charging coils (transmit coil in the charger and receiving coil in the implant) can pose significant challenges in design of the charging apparatus, as it may be difficult to satisfy a combination of engineering and user constraints. In a simple implementation with just one transmitting coil and one receiving coil, the coils may need to be kept in approximate alignment, for optimal coupling, preferably requiring minimal inconvenience and/or interaction for the patient. Sources of misalignment that can occur over time include migration of rotation of the implanted device, and in implementations that utilize a body-worn charger, undesired movement of the charger. Misalignment can be minimized and its effects mitigated to some extent with appropriate design of the coils, devices, and patient-worn accessory that holds the charger, but some patient interaction and compliance may still be required in some implementations.

Some implementations provide feedback to the patient on energy transfer rate and/or coil alignment. The implanted device may provide feedback regarding power received and may transmit the feedback to the external device, which may provide the feedback to the patient in any number of ways. The feedback to the patient may be audible, visual, tactile, or other used singly or in combination. In some implementations, the feedback may be continuously provided, while in other implementations feedback may be provided only if power transfer dips below a predefined level as a warning to inspect and correct the alignment. Some implementations may provide patient feedback based solely on information derived at the external charging device, such as the transmit coil loading, for example.

Some implementations that address coil alignment and power transfer use multiple coils with different orientations or positions in the implanted device, the external charger, or both. As described above, charge or charge reception apparatuses may include multiple coils having orthogonal orientations to facilitate transfer of energy despite wide alignment variations between transmitting and receiving apparatuses. As one example, multiple coils may be used within the charger (or the implanted device), and may be positioned side-by-side to create a larger area for optimal coupling to the implant (charger). In various implementations, output of the multiple coils could be summed, or the highest output coil could be selected via active or passive means. A preferred charger coil may be determined by feedback communicated via telemetry from the implant regarding power transfer as the charger switches between the different transmit coils, according to an implementation. Alternatively, multiple charger coils may be driven out of phase (e.g., 90.degree. out of phase) to create a rotating magnetic field that may be well-received by a single coil in the implant over a variety of orientations. As another alternative, a coil in the implanted device may be rotated on commutated connections, and may include a small magnet to align it with the charge coil in the external device. Such an implementation can include a magnet to provide the alignment force to the implant coil/magnet.

As described above, the implanted device may provide feedback via telemetry to an external charger. In other implementations, the various communications and/or charge energy transfer may occur independently. Implementations that concurrently receive charge energy and transmit information may use energy directly from the charger for powering transfer of the ECG data. For this reason, it may be feasible to use a smaller battery with smaller charge capacity, and the useful life of the battery may be extended. Also, the transfer of data from the implanted device to the external device may be performed at a reduced current level, and may have improved reliability because the charger is already proximal to the implant.

If the required data transmission intervals and charge intervals are similar (e.g. daily), then it may be reasonable to accomplish charging and data transmission concurrently with the devices in close proximity to reduce energy needed for data transfer. Such a system may still include provisions for a longer-range method of bidirectional communication to accomplish a patient activation and transmitted response to activation. In some implementations where charging and data transfer are performed concurrently, the two operations may be performed using the same frequency or harmonics thereof, or they could be performed at separate frequencies. Using separate frequencies may have a regulatory advantage in that, if an ISM frequency is used only for energy transfer and not for communication, it may operate at a higher power than if it is also used for communication. The power would potentially be limited by the Specific Absorption Rate (tissue heating) and not by FCC limits. The communication from the implant for feedback on power transfer and coil orientation could be performed at the same frequency that is used for ECG data transfer, or at a different frequency.

Minimizing the time required to charge the implanted device and maximizing the intervals between charging may improve patient compliance. At the same time, and perhaps in conflict, it may be helpful to align the charge cycle concurrent with (or reminded from) a recurring activity that a typical patient already performs in a predictable cycle. The strongest human cycle is daily, with other cycles including weekly, semi-daily, etc. Another factor in determining an appropriate charge cycle is the cycle required to acquire (upload) data from the device, which may be approximately daily depending on the implant memory size, data compression, and the amount of source data.

Even with implementations where the external charger is body-worn, the charge cycle may be more efficient if the patient is relatively inactive during charge cycles. Examples of appropriate times for charging the implantable device may include during patient sleep, while the patient is seated during a meal, or any time the patient is seated, such as when reading, watching TV, doing office work, or driving a vehicle.

As described above, the external charger may be included in a wearable accessory. Alternatively, the charger may be positioned on the patient (e.g., positioned on the patient's chest while the patient is in a supine position) or adhered to existing clothing. As one example of a wearable accessory that contains and positions the charger, a minimal vest may be provided with the overall positioning accomplished by holes for the neck and at least one arm. Weight and thermal barrier properties of the vest and/charger may be minimized for patient comfort. In some implementations, thermal isolation and/or cooling may be provided between the patient and the charger during charge cycles.

Many variations are possible. For example, the flexible sections may be formed using bellows to provide flexibility for the implanted device. Optionally, a sleeve may be provided over the bellows to prevent tissue ingrowth into the convolutions of the bellows, which may make extracting the device difficult. Referring again to FIG. 23, the device may be implanted such that the end of the device near the telemetry antenna 1045 is the trailing end, and has a shallower implant location versus the end of the device near the battery 1030. This may facilitate improved data telemetry and charge energy transfer.

Various implementations of the device may include interconnecting segments, with at least one of the segments sufficiently hermetic for housing electronic circuits for reliable operation when implanted chronically within a body of a human or animal. In some implementations, other segments of the device may not be substantially hermetic, but may be at least somewhat flexible. Biopotential sense electrodes may be positioned at or near ends of the device. Flexibility provided by the device may make the device more comfortable for the patient, and may improve the contact with tissue relative to a device body that is rigid along its full length. The flexible segments may contain certain functional components of the device such as a communications antennae, recharging apparatus, and battery. The flexible segments may also contain interconnection to connect the sensing electrodes to the rigid section(s) containing the signal processing electronics.

Figure 28:
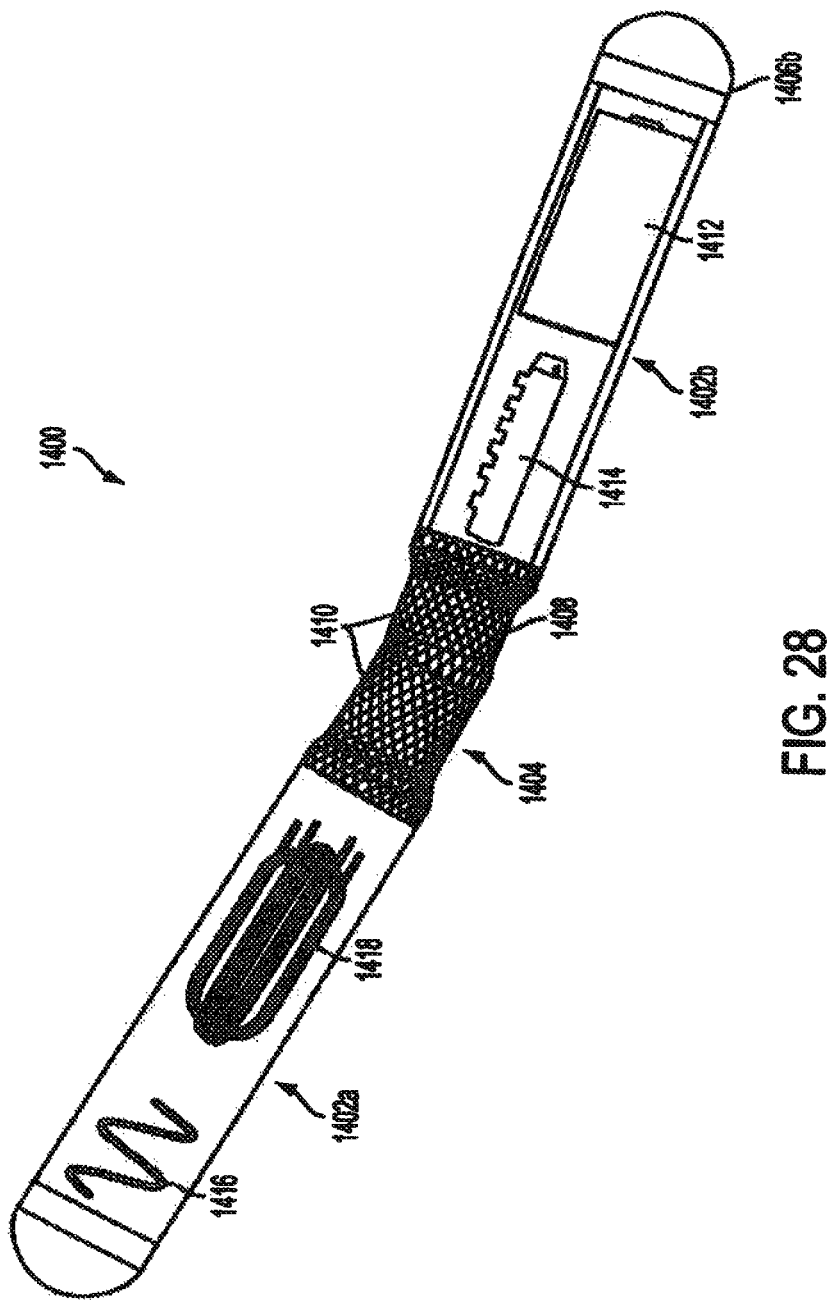
FIG. 28 is a view of an exemplary implantable device with a flexible section that includes a sleeve of wire braid or mesh.

FIG. 28 is a cutaway view of an implementation of an implantable device 1400 that includes two rigid sections 1402 separated by a flexible section 1404. The device 1400 includes rounded electrodes 1406 at opposing longitudinal ends of the device. The flexible section 1404 includes a sleeve 1408 of wire braid or mesh, which may add strength to the flexible section 1401 or may prohibit flexure beyond a predetermined angle. For example, the sleeve 1408 may limit flexure o the flexible section to an angle 1410 (or less in some implementations), as shown. The example shows a particular angle 1410, but larger or smaller angles are possible by modifying flexure properties of the sleeve 1408. In some implementations, the sleeve may be embedded with the material comprising the flexible section, for example, or may alternatively be place over top of the section. A battery 1412 and an electronics module 1414 are shown within one of the rigid sections 1402b, and a telemetry antenna 1416 and a charge reception apparatus 1418 are shown in the other rigid section 1402a. In implementations having multiple flexible sections, some or all of the flexible sections may include a sleeve similar to sleeve 1408, and in some cases sleeves having differing flexure properties may be used on flexible sections (e.g., on different flexible sections) of the same device. As such, device implementations with two or more flexible sections where a first flexible section is limited to a first angle of deflection and a second flexible section is limited to a second angle of deflection, different from the first angle of deflection, are possible.

A layer of tissue, referred to as fascia, covers the pectoral muscle. In some implementations, any of the devices discussed herein (e.g., devices 100, 200, 1010, 1100, 1200, 1300, 1400) may be introduced to a sub-fascial implant location. In some cases, introducing the device to a sub-fascial location may reduce a risk of erosion and may provide a more stable implant location. In some implementations, the device may be implanted such that the entire device remains above the pectoral fascia. In alternative implementations, the fascia may be penetrated and the device may be implanted such that the entire device is located below the pectoral fascia. In yet other implementations, the fascia may be penetrated and the device may be implanted such that a distal portion of the device is positioned below the fascia and a proximal portion of the device is positioned above the fascia.

A number of implementations have been described. Nevertheless, it will be understood that various modifications may be made without departing from the spirit and scope of the techniques, devices, and systems discussed herein.

What is claimed is:

1. An introducer system for implanting an implantable medical device at a subcutaneous location within a body of a patient, the introducer system comprising:
   a) an insert extending from a distal insert portion having a closed distal insert end to a proximal insert end, wherein at least a portion of the insert is sized and shaped to match at least a portion of the implantable medical device; and
   b) a sheath, comprising:
      i) a first leg extending from a distal first leg end to a proximal first finger grip;
      ii) a second leg extending from a distal second leg end to a proximal second finger grip;
      iii) an intermediate tapered portion extending distally and inwardly toward a longitudinal axis for at least a portion of its length from an open proximal tapered portion end to an open distal tapered portion end, wherein the distal first and second leg ends, opposite the respective finger grips, are connected at spaced apart locations to the open proximal tapered portion end; and
      iv) a distal sheath portion defining a sheath lumen extending along the longitudinal axis from the open distal tapered portion end to an open distal sheath portion end thereof,
      v) wherein the intermediate and distal sheath portions define an opening sized to separately house the insert and at least a portion of the implantable medical device,
   c) wherein with the insert received in the sheath, the closed distal insert end extends distally out past the open distal sheath end with the proximal insert end being proximal the open proximal tapered portion end so that the proximal insert end is manipulatable in a distal direction to move the insert and the sheath distally through the body to a desired implant location, and wherein the open proximal sheath end permits removal of the insert from the sheath to thereby provide for moving the implantable medical device through the open proximal sheath end and into the tapered intermediate portion and the distal sheath portion, and
   d) wherein the first and second finger grips are manipulatable to move their respective first and second legs from a first position relatively closely spaced to each other to a second position of a greater distance from each other than the first position to thereby separate the intermediate tapered and distal portions of the sheath into a first split portion connected to the first leg and its finger grip and a second split portion connected to the second leg and its finger grip to thereby facilitate removal of the sheath from the subcutaneous implant location while leaving the medical device implanted in the body.

2. The introducer system of claim 1 wherein the distal sheath portion is sized and shaped in proportion to receive the corresponding distal insert portion therein.

3. The introducer system of claim 1 wherein the distal sheath portion is more flexible than the distal insert portion.

4. The introducer system of claim 3 wherein the distal insert portion has sufficient rigidity to avoid substantial deflection when directed through a fatty tissue layer of the patient, but sufficient flexibility to, upon contacting a surface of a muscle layer of the patient, deflect and slide across the surface of the muscle layer without penetrating the muscle layer.

5. The introducer system of claim 1 wherein an external surface of the intermediate tapered and distal sheath portions includes diametrically opposed surface modifications extending from the open proximal tapered portion to the open distal sheath portion end, the surface modifications reducing a tensile strength of the sheath to facilitate manipulation of the sheath into the first and second split portions.

6. The introducer system of claim 1 wherein the semi-flexible insert defines a cavity sized and shaped to receive a rod member preformed to define an arc angle, and wherein the rod member is more rigid than the insert.

7. The introducer system of claim 1 wherein the proximal insert end is closed.

8. The introducer system of claim 1 wherein with the insert received in the sheath, the proximal insert end is proximal the open proximal tapered portion end, but distal the first and second finger grips.

9. The introducer system of claim 1 wherein the first and second legs of the sheath extend proximally along the longitudinal axis away from the intermediate tapered portion.

10. The introducer system of claim 1 wherein the intermediate tapered portion of the sheath comprises a first tapered sheath section widening linearly and proximally along the longitudinal axis from a first width at the open distal tapered portion end to a second, wider width meeting a constant width section of the intermediate portion and then to a second tapered sheath section extending proximally along the longitudinal axis from a third width to a fourth, wider width at the open proximal tapered portion end of the sheath.

11. The introducer system of claim 10 wherein at least a portion of the second tapered sheath section extends arcuately and proximally along the longitudinal axis from the third width to the fourth, wider width at the open proximal tapered portion end of the sheath.

12. The introducer system of claim 1 wherein the first finger grip is substantially aligned along a first imaginary plane and the second finger grip is substantially aligned along a second imaginary plane parallel to the first imaginary plane and wherein a third imaginary plane bisects the intermediate tapered portion and the distal portion of the sheath, the third imaginary plane being aligned substantially perpendicular to the first and second imaginary parallel planes.

13. A sheath, comprising:
a) a first leg extending from a distal first leg end to a proximal first finger grip;
b) a second leg extending from a distal second leg end to a proximal second finger grip;
c) an intermediate tapered portion extending distally and inwardly toward a longitudinal axis for at least a portion of its length from an open proximal tapered portion end to an open distal tapered portion end, wherein the distal first and second leg ends, opposite the respective finger grips, are connected at spaced apart locations to the open proximal tapered portion end, d) wherein the first finger grip is substantially aligned along a first imaginary plane and the second finger grip is substantially aligned along a second imaginary plane parallel to the first imaginary plane and wherein a third imaginary plane bisects the intermediate tapered portion and the distal portion of the sheath, the third imaginary plane being aligned substantially perpendicular to the first and second imaginary parallel planes; and
e) a distal sheath portion defining a sheath lumen extending along the longitudinal axis from the open distal tapered portion end to an open distal sheath portion end thereof,
e) wherein the intermediate and distal sheath portions define an opening sized to separately house an insert and at least a portion of an implantable medical device, and
f) wherein the first and second finger grips are manipulatable laterally along the third imaginary plane to move their respective first and second legs from a first position relatively closely spaced to each other to a second position of a greater distance from each other than the first position to thereby separate the intermediate tapered and distal portions of the sheath into a first split portion connected to the first leg and its finger grip and a second split portion connected to the second leg and its finger grip.

14. The sheath of claim 13 wherein an external surface of the intermediate tapered and distal sheath portions includes diametrically opposed surface modifications extending from the open proximal tapered portion to the open distal sheath portion end, the surface modifications reducing a tensile strength of the sheath to facilitate manipulation of the sheath into the first and second split portions.

15. The sheath of claim 13 wherein the first and second legs extend proximally along the longitudinal axis away from the intermediate tapered portion.

16. The sheath of claim 13 wherein the intermediate tapered portion comprises a first tapered sheath section widening linearly and proximally along the longitudinal axis from a first width at the open distal tapered portion end to a second, wider width meeting a constant width section of the intermediate portion and then to a second tapered sheath section extending proximally along the longitudinal axis from a third width to a fourth, wider width at the open proximal tapered portion end of the sheath.

17. An introducer system for implanting an implantable medical device at a subcutaneous location within a body of a patient, the introducer system comprising:
a) an insert extending from a distal insert portion having a closed distal insert end to a closed proximal insert end, wherein at least a portion of the insert is sized and shaped to match at least a portion of the implantable medical device; and
b) a sheath, comprising:
i) a first leg extending from a distal first leg end to a proximal first finger grip;
ii) a second leg extending from a distal second leg end to a proximal second finger grip;
iii) an intermediate tapered portion comprising a first tapered sheath section widening linearly and proximally along a longitudinal axis from a first width at an open distal tapered portion end to a second, wider width meeting a constant width section of the intermediate portion and then to a second tapered sheath section extending proximally along the longitudinal axis from a third width to a fourth, wider width at an open proximal tapered portion end of the sheath, iv) wherein the distal first and second leg ends, opposite the respective finger grips, are connected at spaced apart locations to the open proximal tapered portion end; and v) a distal sheath portion defining a sheath lumen extending along the longitudinal axis from the open distal tapered portion end to an open distal sheath portion end thereof, vi) wherein the intermediate and distal sheath portions define an opening sized to separately house the insert and at least a portion of the implantable medical device, c) wherein with the insert received in the sheath, the closed distal insert end extends distally out past the open distal sheath end with the proximal insert end being proximal the open proximal tapered portion end so that the closed proximal insert end is manipulatable in a distal direction to move the insert and the sheath distally through the body to a desired implant location, and wherein the open proximal sheath end permits removal of the insert from the sheath to thereby provide for moving the implantable medical device through the open proximal sheath end and into the tapered intermediate portion and the distal sheath portion, and d) wherein the first and second finger grips are manipulatable to move their respective first and second legs from a first position relatively closely spaced to each other to a second position of a greater distance from each other than the first position to thereby separate the intermediate tapered and distal portions of the sheath into a first split portion connected to the first leg and its finger grip and a second split portion connected to the second leg and its finger grip to thereby facilitate removal of the sheath from the subcutaneous implant location while leaving the medical device implanted in the body.

18. The introducer system of claim 17 wherein at least a portion of the second tapered sheath section extends arcuately and proximally along the longitudinal axis from the third width to the fourth width.

19. The introducer system of claim 17 wherein the first finger grip is substantially aligned along a first imaginary plane, the second finger grip is substantially aligned along a second imaginary plane parallel to the first imaginary plane, and a third imaginary plane bisects the intermediate tapered portion and the distal portion of the sheath, and wherein the third imaginary plane is aligned substantially perpendicular to the first and second imaginary parallel planes.

20. The introducer system of claim 17 wherein with the insert received in the sheath, the proximal insert end is proximal the open proximal tapered portion end, but distal the first and second finger grips.

* * * * *